United States Patent
Zhao et al.

(10) Patent No.: US 10,902,713 B2
(45) Date of Patent: Jan. 26, 2021

(54) SYSTEM FOR PREDICTING EGRESS FROM AN OCCUPANT SUPPORT

(71) Applicants: HILL-ROM SERVICES, INC., Batesville, IN (US); Chunhui Zhao, Zhejiang (CN); Limin Lu, Zhejiang (CN)

(72) Inventors: Chunhui Zhao, Zhejiang (CN); Limin Lu, Zhejiang (CN); Yongji Fu, Batesville, IN (US); Eric D. Agdeppa, Batesville, IN (US); David Lance Ribble, Batesville, IN (US); Kirsten M. Emmons, Batesville, IN (US)

(73) Assignee: Hill-Rom Services, Inc., Batesville, IN (US)

( * ) Notice: Subject to any disclaimer, the term of this patent is extended or adjusted under 35 U.S.C. 154(b) by 0 days.

(21) Appl. No.: 16/343,447

(22) PCT Filed: Oct. 23, 2017

(86) PCT No.: PCT/US2017/057823
§ 371 (c)(1),
(2) Date: Apr. 19, 2019

(87) PCT Pub. No.: WO2018/080971
PCT Pub. Date: May 3, 2018

(65) Prior Publication Data
US 2019/0266870 A1    Aug. 29, 2019

Related U.S. Application Data

(60) Provisional application No. 62/411,871, filed on Oct. 24, 2016.

(51) Int. Cl.
*A61B 5/11* (2006.01)
*G08B 21/02* (2006.01)
(Continued)

(52) U.S. Cl.
CPC ............ *G08B 21/02* (2013.01); *A61B 5/1115* (2013.01); *A61B 5/6892* (2013.01);
(Continued)

(58) Field of Classification Search
CPC ....... A61B 5/1115; A61B 5/1113; A61B 5/11; A61B 5/1118; A61B 5/002; A61B 5/1116;
(Continued)

(56) References Cited

U.S. PATENT DOCUMENTS

| | | | |
|---|---|---|---|
| 5,276,432 A | 1/1994 | Travis | |
| 6,067,019 A * | 5/2000 | Scott | A61B 5/11 340/562 |

(Continued)

OTHER PUBLICATIONS

European Search Report for EP Application 17864647.7; dated Jul. 19, 2019; Place of search—The Hague; Date of completion of the search—Jul. 10, 2019.

(Continued)

*Primary Examiner* — Benyam Haile
(74) *Attorney, Agent, or Firm* — Barnes & Thornburg LLP

(57) ABSTRACT

A system for predicting exit from an occupant support, includes a processor, a memory in communication with the processor, and a frame having at least one force sensor which outputs a force signal in response to force exerted thereon. The system also includes machine readable instructions stored in the memory which cause the system to perform at least the following actions when executed by the processor: 1) determine a property of the signal during an interval of time, 2) classify the property as suggesting an exit event or as not suggesting an exit event, and 3) if the property is classified as suggesting an exit event, generate a notification thereof.

17 Claims, 23 Drawing Sheets

(51) Int. Cl.
*A61G 7/05* (2006.01)
*A61B 5/00* (2006.01)
*G08B 21/22* (2006.01)
*A61G 12/00* (2006.01)

(52) U.S. Cl.
CPC .......... *A61B 5/7264* (2013.01); *A61B 5/7282* (2013.01); *A61B 5/746* (2013.01); *A61G 7/0506* (2013.01); *A61G 7/0519* (2016.11); *A61G 12/00* (2013.01); *G08B 21/22* (2013.01); *A61B 2505/00* (2013.01); *A61B 2562/0252* (2013.01); *A61G 2203/32* (2013.01)

(58) Field of Classification Search
CPC ............ G08B 21/0438; G08B 21/0461; G08B 21/0423
See application file for complete search history.

(56) References Cited

U.S. PATENT DOCUMENTS

| | | |
|---|---|---|
| 6,208,250 B1 | 3/2001 | Dixon et al. |
| 7,699,784 B2 | 4/2010 | Wan Fong et al. |
| 8,405,510 B2 | 3/2013 | Shieh et al. |
| 2005/0115561 A1* | 6/2005 | Stahmann ............ A61B 5/0031 128/200.24 |
| 2008/0091121 A1* | 4/2008 | Sun ...................... A61B 5/0059 600/587 |
| 2008/0169931 A1* | 7/2008 | Gentry .................. A61B 5/1113 340/573.1 |
| 2009/0119843 A1 | 5/2009 | Rodgers et al. |
| 2009/0260158 A1* | 10/2009 | Kazuno ................. A61B 5/1115 5/600 |
| 2011/0156915 A1 | 6/2011 | Brauers et al. |
| 2012/0056747 A1 | 3/2012 | Stadlthanner et al. |
| 2012/0259248 A1 | 10/2012 | Receveur |
| 2013/0197375 A1* | 8/2013 | Heise ..................... A61B 5/024 600/484 |
| 2016/0005289 A1 | 1/2016 | Ribble et al. |
| 2016/0022218 A1 | 1/2016 | Hayes et al. |
| 2016/0063846 A1 | 3/2016 | Lemire et al. |
| 2016/0128610 A1 | 5/2016 | Kostic et al. |

OTHER PUBLICATIONS

PCT Search Report and Written Opinion prepared for PCT/US2017/057823, completed Dec. 21, 2017.
Response to European Search Report for EP Application 17864647.7; dated Jan. 9, 2020.
Communication pursuant to Article 94(3) EFC dated Jul. 24, 2020 for European Patent Application No. 17864647.7; 5 pages.
Notification of Reasons for Rejection dated Sep. 29, 2020 for Japanese Patent Application No. 2019-543180; 7 pages.

* cited by examiner

SYSTEM FOR PREDICTING EGRESS FROM AN OCCUPANT SUPPORT

CROSS-REFERENCE TO RELATED APPLICATIONS

This application is a US national stage entry of International Application PCT/US2017/057823 (international filing date Oct. 23, 2017) which claims priority under 35 U.S.C. § 119(e) to U.S. Provisional Application Ser. No. 62/411,871, filed Oct. 24, 2016, the contents of both of which are incorporated herein by reference in their entirety.

TECHNICAL FIELD

The subject matter described herein relates to systems and methods for predicting unauthorized egress or exit of an occupant from an occupant support. In one example the occupant support is a hospital bed.

BACKGROUND

Beds such as those used in hospitals, other health care facilities and sometimes in home care settings may be equipped with a bed exit prediction and alarm system. Such systems predict whether an occupant of the bed is intent on exiting the bed and, if so, issue a local or remote warning such as a local alarm or a signal to a hospital nurses' station. One example system for predicting bed exit is described in U.S. Pat. No. 6,208,250. Such systems are especially useful if the occupant is not authorized to exit the bed without assistance. However exit prediction and alarm systems can produce false alarms. These alarms, like legitimate alarms, require a caregiver response and therefore place an undue burden on the caregiver staff. It is, therefore, of interest to develop systems which accurately predict actual bed exit while reducing the likelihood of false alarms.

Some beds may include sensors such as load cells for determining the occupant's weight. To the extent that output signals from these sensors can also be used to help predict bed exit, the cost and complexity of the bed can be reduced. Therefore it is of interest to use force readings from the weight sensors for the additional purpose of predicting bed exit.

SUMMARY

A system for predicting exit from an occupant support includes a processor, a memory in communication with the processor, and an occupant support frame having at least one force sensor which outputs a force signal in response to force exerted thereon. Machine readable instructions are stored in the memory. When executed by the processor the machine readable instructions cause the system to determine a property of the force signal during an interval of time, to classify the signal property as suggesting an exit event or as not suggesting an exit event, and, if the property is classified as suggesting an exit event, generate a notification thereof.

BRIEF DESCRIPTION OF THE DRAWINGS

The foregoing and other features of the various embodiments of the exit prediction system described herein will become more apparent from the following detailed description and the accompanying drawings in which.

DETAILED DESCRIPTION

Figure 1:
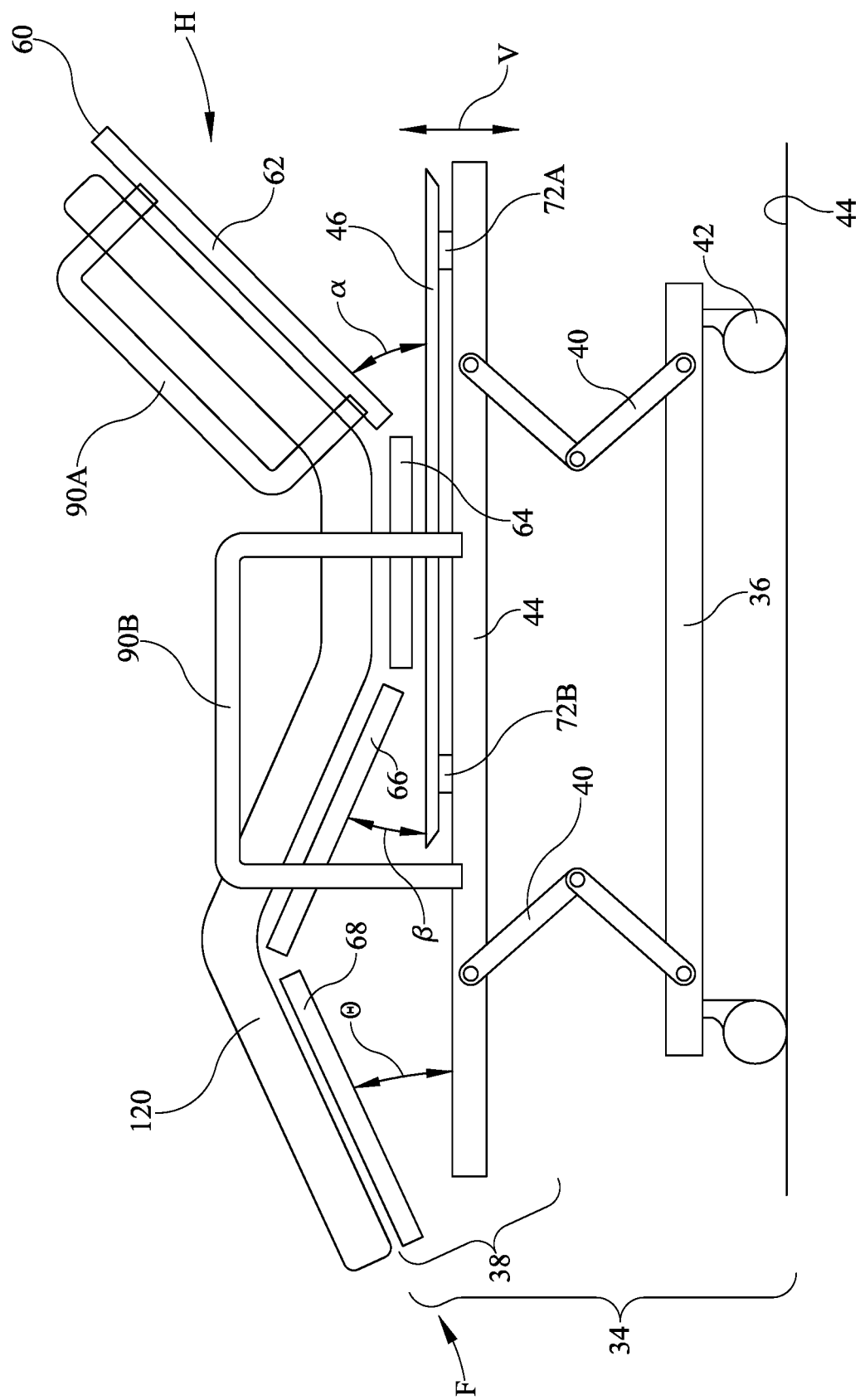
FIG. 1 is a left side elevation view of a hospital bed, shown highly simplified, with articulable deck sections at nonzero angular orientations.

In this specification features the same as or similar to features already described may be identified by reference numerals the same as or similar to those already used.

Figure 2:
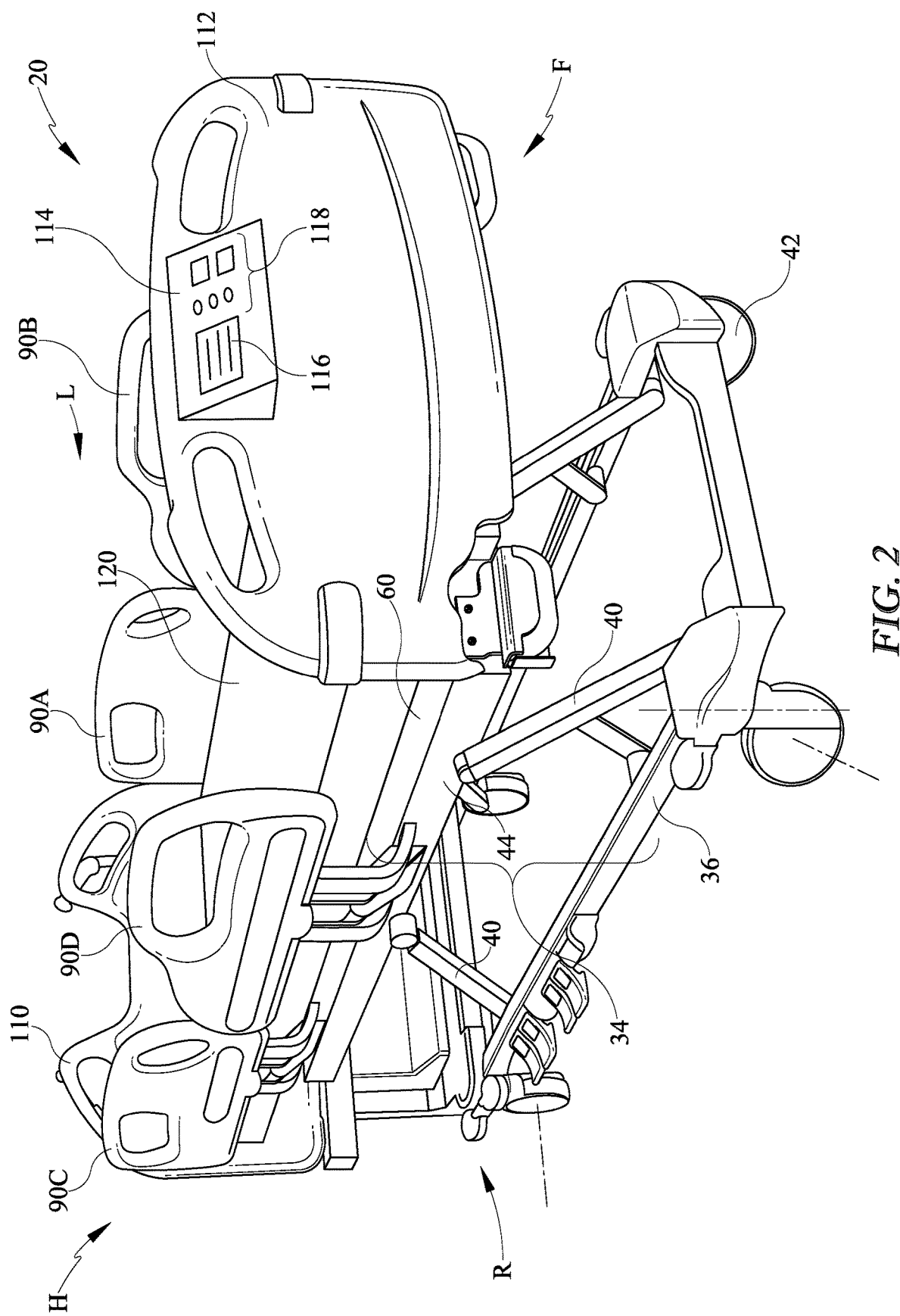
FIG. 2 is a perspective view of a hospital bed, more realistic than the view of FIG. 1.
Figure 3:
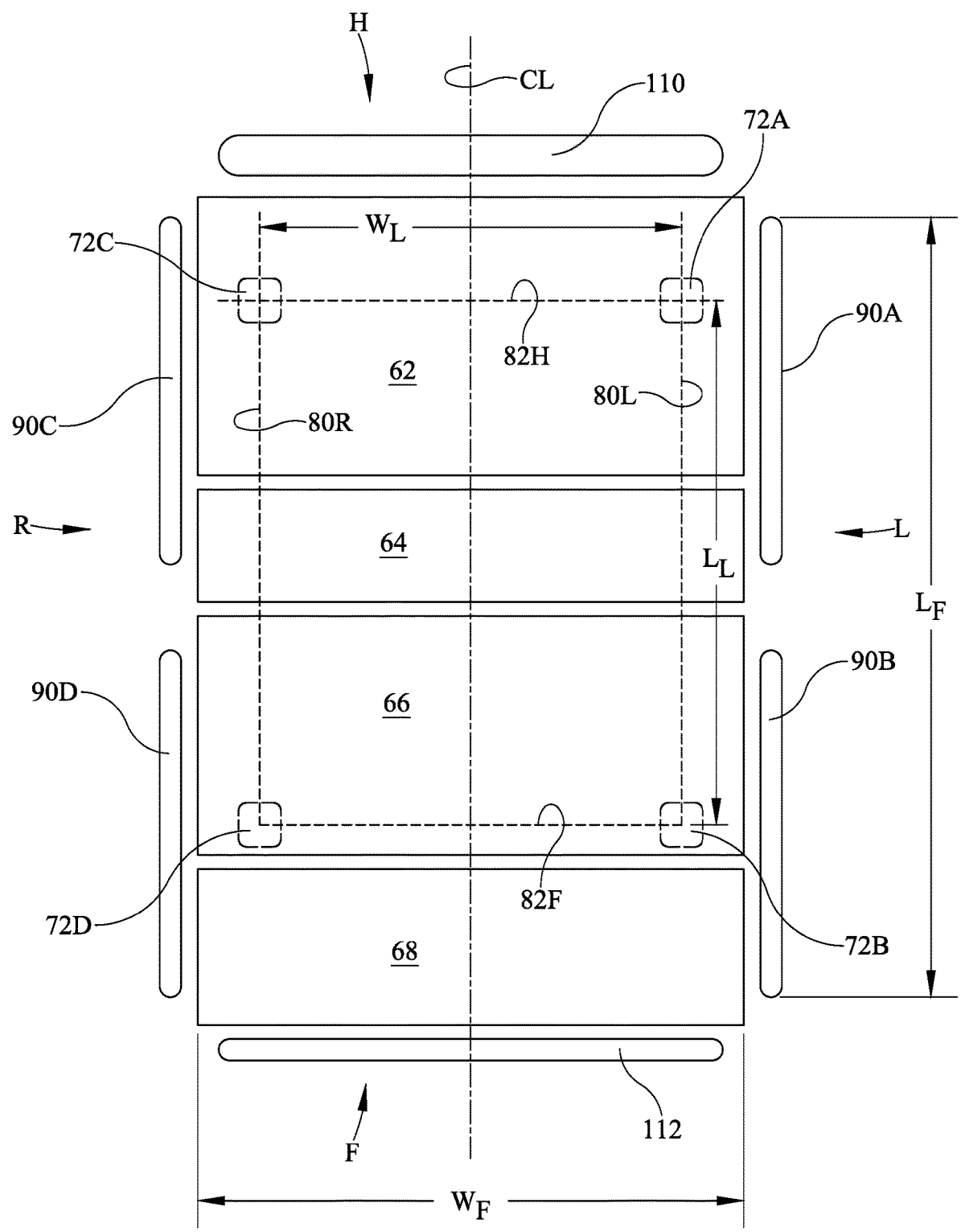
FIG. 3 is a plan view of a hospital bed, shown highly simplified, with articulable deck sections each shown at an angular orientation of zero degrees and also showing four load cells.

FIGS. 1-3 illustrate an occupant support such as a hospital bed 20. Bed 20 includes a frame 34 comprised of a base frame 36 and an elevatable frame 38 which is supported on the base frame by supports 40 and is vertically moveable relative to the base frame as indicated by directional arrow V in FIG. 1. The bed extends longitudinally from a head end H to a foot end F and laterally from a left side L to a right side R, where left and right are taken from the perspective of a supine patient or occupant. Frame 34 includes casters 42 extending from the base frame to floor 44. FIG. 3 also shows a longitudinally extending bed centerline CL.

The elevatable frame 38 includes a sub-frame 44, a weigh frame 46 and a deck generally indicated by 60. The illustrated deck is a segmented deck which includes an upper body or torso section 62 corresponding approximately to a supine occupant's torso, a seat section 64 corresponding approximately to the occupant's buttocks, a thigh section 66 corresponding approximately to the occupant's thighs and a calf section 68 corresponding approximately to the occupant's calves and feet. As seen in the FIG. 1 the torso, thigh and calf sections are orientation adjustable from 0 degrees (parallel to the sub-frame) to a nonzero orientation in order to change the profile of the bed.

A mattress 120 rests on the deck. The mattress is flexible enough to conform to the deck profile as the orientations of the deck sections are adjusted.

The frame includes one or more force sensors, designated collectively by 72, interposed between weigh frame 46 and sub-frame 44. The illustrated force sensors are an upper left load cell 72A, a lower left load cell 72B, an upper right load cell 72C, and a lower right load cell 72D. The designation "upper" means more headwardly. The designation "lower" means more footwardly. The load cells are arranged in a substantially rectangular pattern. The load cells transfer the weight of the weigh frame, the weight of bed components and other articles supported by the weigh frame, and the weight of an occupant of the bed to sub-frame 44. Each load cell outputs a force signal in response to the force exerted on it. The force signals may be zeroed prior to a patient entering the bed so that the signals represent only the patient's weight and actions attributable to the patient but exclude all other forces exerted on the load cells such as the weight of the weigh frame and deck. Although the force signals are electrical signals, they represent the weight or force exerted on each load cell and therefore, in the interest of simplicity, are referred to herein as weight or force signals.

The frame has a longitudinal length or longitudinal dimension $L_F$ and a lateral width or lateral dimension $W_F$. The dimension $L_F$ is the longitudinal length of the deck measured horizontally when each of the deck sections is at its minimum angle of orientation ($\alpha=\beta=\theta=0$). The dimension $W_F$ is the lateral width of the deck.

The bed also includes a left siderail assembly comprising at least one left siderail mounted on the left side of the frame and a right siderail assembly comprising at least one right siderail mounted on the right side of the frame. In the illustrated embodiment of FIGS. 2-3 the left siderail assembly comprises an upper left siderail 90A and a lower left siderail 90B. The right siderail assembly comprises an upper right siderail 90C, and a lower right siderail 90D. The designation "upper" means more headwardly. The designation "lower" means more footwardly.

The upper siderails are connected to upper body deck section 62 and therefore rotate with the upper body deck section as that section rotates through angle $\alpha$ (FIG. 1). The lower siderails are connected to a portion of the elevatable frame that does not rotate about a laterally extending axis. Therefore the lower siderails are always at a fixed orientation relative to subframe 44 as seen in side elevation.

Each siderail is positionable at a deployed position or elevation at which its upper edge is higher than the top of the mattress and at a stowed position or elevation at which its upper edge is lower than the top of the mattress so that the occupant can enter and exit the bed. In FIG. 2 all four siderails are deployed. In FIG. 3 the shading applied to the upper siderails signifies that those siderails are deployed; the lack of shading on the lower siderails signifies that those siderails are stowed. On some beds the siderails may also be positionable at intermediate positions, neither as high as the deployed position nor as low as the stowed position.

The positions of the siderails, taken collectively, define a siderail configuration. Certain siderail configurations, such as one in which all four siderails are deployed, may be designated as exit-deterring configurations. Other configurations, such as one in which all four siderails are stowed, may be designated as exit accommodating configurations. Other combinations of deployed positions, stowed positions and intermediate positions (if intermediate positions are available) may be designated as exit deterring or exit accommodating configurations. Alternatively or additionally the exit deterring or exit accommodating potential of the siderial configurations may be graduated. For example on a scale of zero to one hundred, where zero signifies a highly exit deterrent configuration and 100 signifies a highly exit accommodating configuration, the "all-deployed" configuration might be assigned the value of zero while the all-stowed configuration might be assigned a value of 100. Other configurations may be assigned other values in the zero to one hundred range depending on their perceived potential for deterring or accommodating egress. The extent to which a siderail configuration is considered to be exit deterrant or exit accommodating may be subject to judgement. For example, a bed with all four siderails stowed may be less exit accommodating than a bed with the foot siderails stowed and the head siderails deployed. This is because a patient in a bed with the latter configuration can use the deployed siderials to support himself while exiting from the bed, and therefore may be more inclined to attempt an unauthorized exit.

The bed also includes a headboard 110 and a footboard 112. The illustrated footboard is installable on and removable from the foot end of the frame, without special tools or skills, in order to accommodate occupant egress from the foot end of the bed. For example some beds can be adjusted so that their profile mimics that of a chair. When a user places the bed in its chair-like profile it is customary to remove the footboard in order to give the occupant the ability to step out of the bed/chair.

The bed also includes a user interface, 114 shown on footboard 112 (FIG. 2). In general the user interface includes a display 114 for displaying information, and user input acceptors 118 such as buttons, switches or a keyboard for accepting user inputs.

Figure 4:
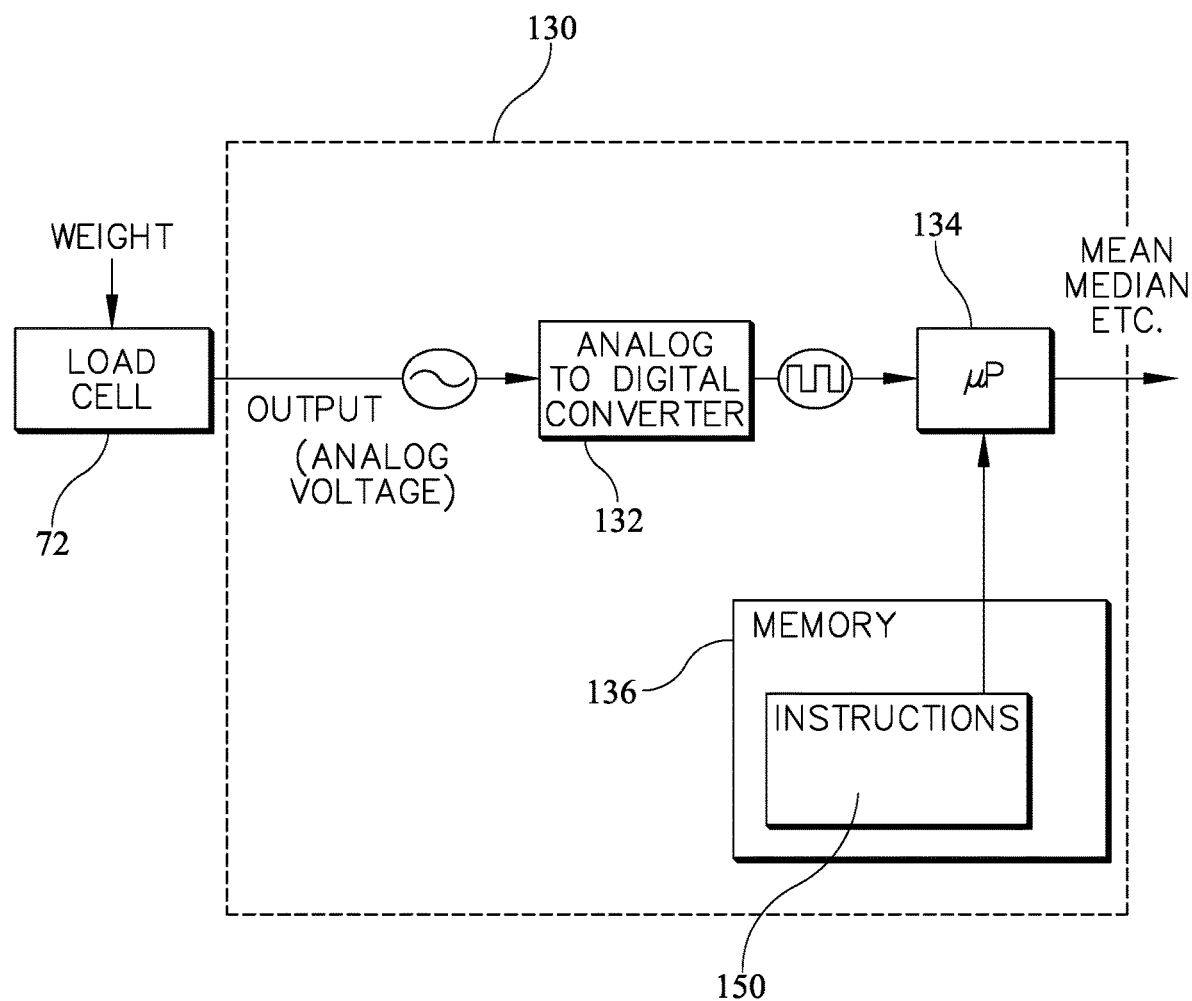
FIG. 4 is a schematic view showing a suite of components used in the predictive system described herein including a processor and a memory containing machine readable and machine executable instructions.

Referring to FIG. 4, the exit prediction system described herein includes a suite of components 130 which include an analog to digital (A/D) converter, 132 a processor 134, and a memory 136 in communication with the processor. The memory contains machine readable instructions 150 executable by the processor. FIG. 4 suggests physical connections between the components however wireless connections may be employed if desired. For example the processor could be a remote computer and/or the memory could be a remotely located server.

Figure 5:
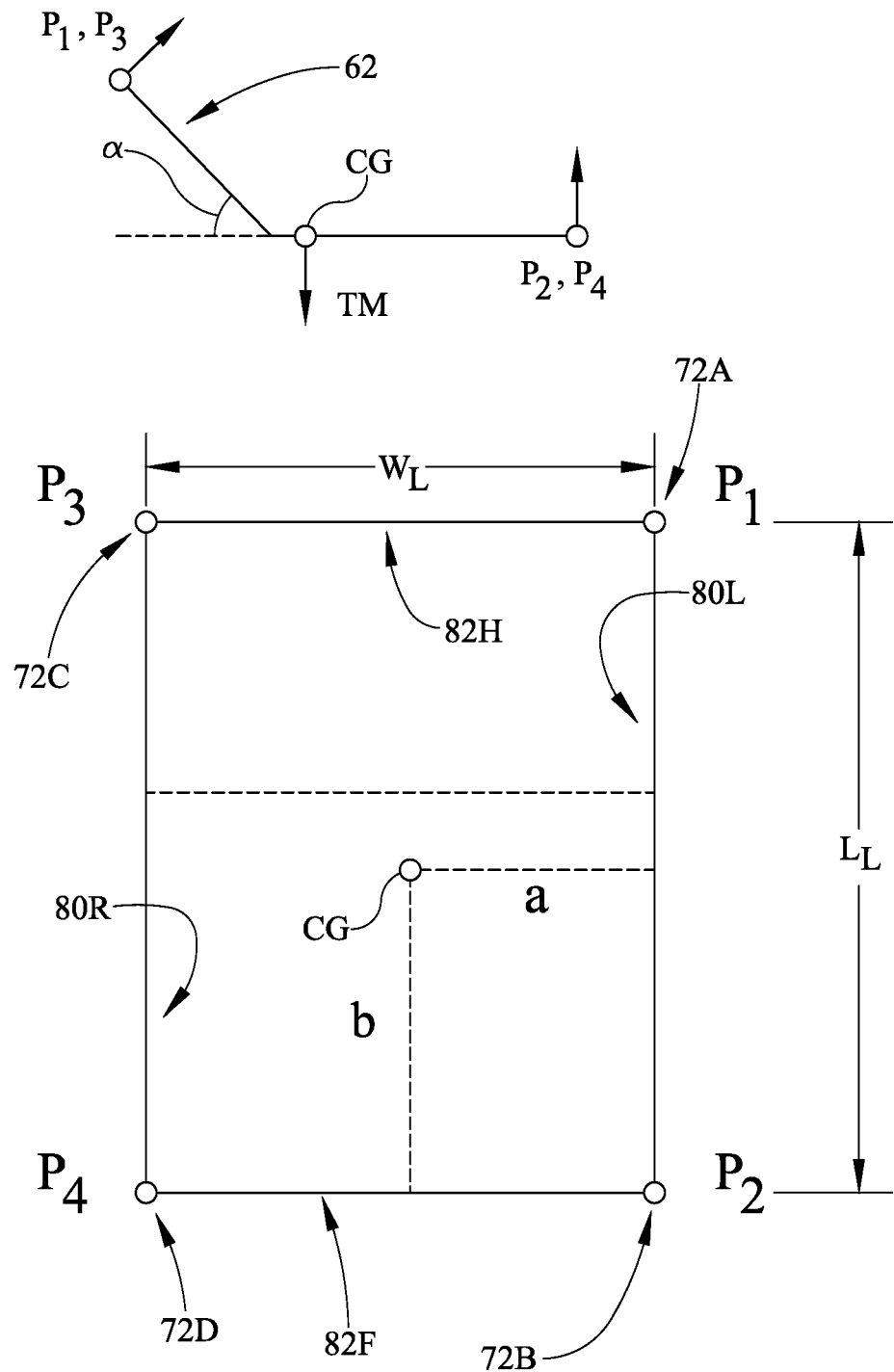
FIG. 5 is a schematic, right side elevation view and a schematic plan view showing the load cells of FIG. 3.

Referring to FIG. 5, the machine readable instructions 150 include a group of instructions which cause the system to determine the location of the occupant's center of gravity, CG. Knowledge of the lateral coordinate of the center of gravity, a, indicates the occupant's position relative to the left and right edges of the bed and therefore is instrumental in helping to predict if the occupant is intent on exiting the bed from one of the sides. As shown, a is measured from a notional line 80L extending between the sensing elements of left side load cells 72A, 72B, but could instead be measured from a notional line 80R extending between the sensing elements of right side load cells 72C, 72D. Knowledge of the longitudinal coordinate of the center of gravity, b, indicates the occupant's position relative to the head end and foot end of the bed and therefore is instrumental in helping to predict if the occupant is intent on exiting the bed from its head or foot end. As shown, b is measured from a notional line 82F extending between the sensing elements of foot end load cells 72B, 72D, but could instead be measured from a notional line 82H extending between the sensing elements of head end load cells 72A, 72C. The likelihood of the occupant exiting from the head end of the bed is remote due to the presence of the headboard and the fact that the head end of the bed is typically placed near a wall of the facility. The likelihood of the occupant exiting from the foot end of the bed is greater, especially if the footboard has been removed, but is also relatively small. Accordingly, it may be sufficient to consider only the likelihood of occupant exit from the left and right sides, in which case knowledge of the longitudinal location b of the occupant's CG is not required.

Referring principally to FIGS. 3 and 5, the longitudinal distance between the sensing elements of load cells 72A and 72B or between the sensing elements of load cells 72C and 72D is $L_L$. The lateral distance between the sensing elements of load cells 72A and 72C or between the sensing elements of load cells 72B and 72D is $W_L$. The lateral coordinate of the center of gravity, a, is measured from a notional line 80L extending between the sensing elements of left side load cells 72A, 72B. The longitudinal coordinate of the center of gravity, b, is measured from a notional line 82F extending between the sensing elements of foot end load cells 72B, 72D. Angle α is the orientation angle of torso deck section 62 which is also seen in FIG. 1. TM is the patient's weight and is shown acting through the patient's center of gravity CG. P1, P2, P3 and P4 are the output signals from load cells 72A, 72B, 72C, 72D respectively. Although these are electrical signals, they represent the force exerted on each load cell and therefore in the interest of simplicity are referred to herein as force signals. If the bed occupant is substantially at rest, the sum of the force signals equals the patient's weight and therefore may be referred to as a weight signal.

Figure 6:
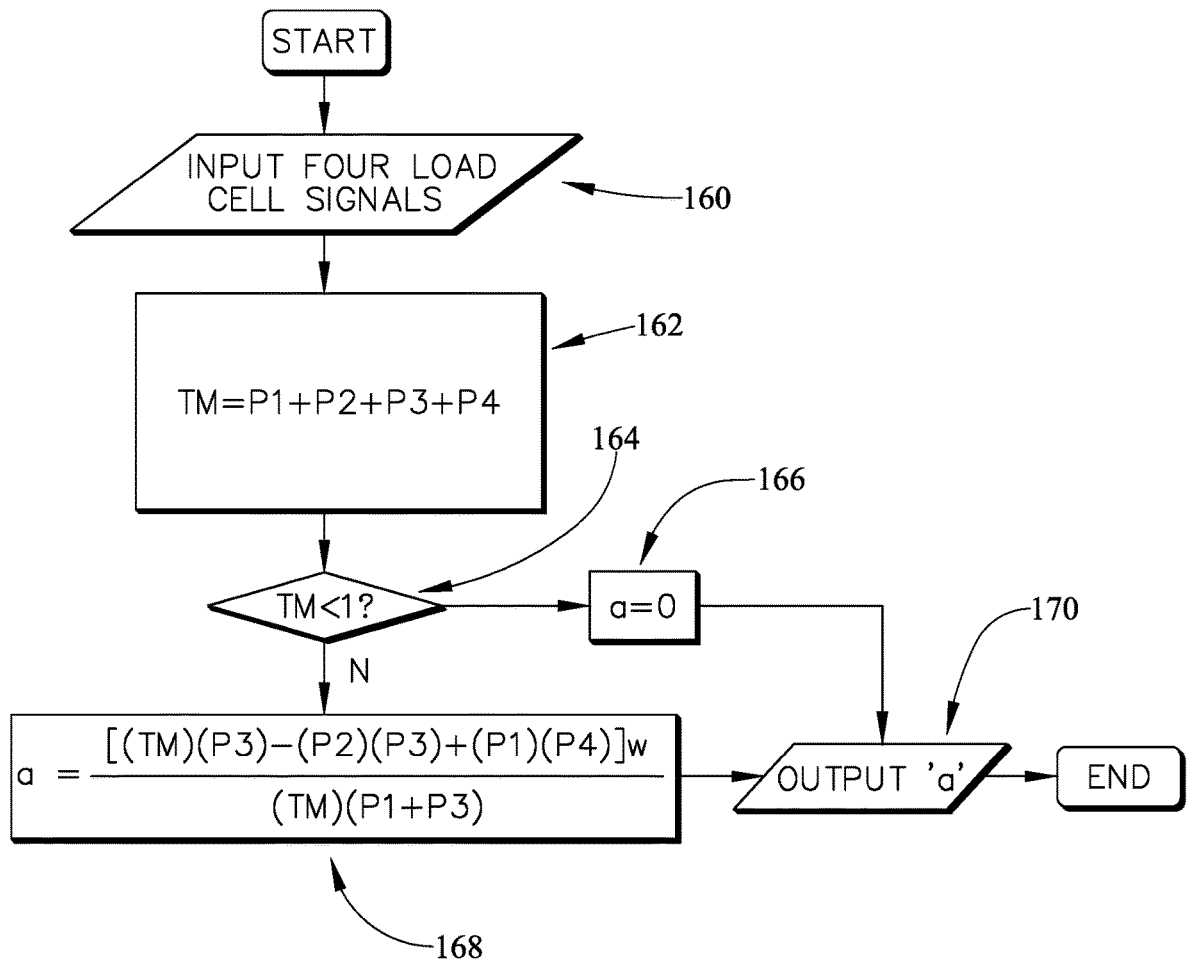
FIG. 6 is a block diagram illustrating a procedure by which the machine readable instructions determine the lateral coordinate a of a bed occupant's center of gravity.

Referring additionally to FIG. 6, at block 160 the processor receives the four load cell signals. The signals shown in the diagram are zeroed signals, i.e. signals that represent only the occupant's weight and other forces attributable to the occupant, not the weight of any other bed components such as weigh frame 46, deck 60 and mattress 120 or other articles which might have been placed on the bed such that their weight would be transferred to the ground by way of the load cells. Provided the occupant is essentially at rest the sum of the forces acting on the load cells substantially equals the occupant's weight. Block 162 calculates the sum of the forces to determine a total weight TM. Block 164 compares TM to a number so small that it corresponds to the absence of an occupant's weight. In the example of the block diagram the small number is 1.0 (e.g. 1 kg). If, at block 164, it is determined that TM is less than the small number (indicating that the bed is unoccupied) the procedure advances to block 166 where a, the lateral coordinate of the CG, is set to zero (otherwise the denominator at block 168, described below, would be zero). The value of zero for the lateral coordinate a of the CG signifies that the bed is unoccupied because it corresponds to a location at or near the left edge of the bed. A similar determination could be carried out for longitudinal coordinate b, however one or the other is sufficient.

However if it is determined at block 164 that TM is not less than the small number (indicating that the bed is occupied) the procedure advances to block 168 where a nonzero value of the lateral coordinate a of the CG is calculated as will now be described. In practical applications, almost all the sensors are affected by random measurement noise. In order to remove the noise and preserve information at the same time, median filtering is carried out as the first step to deal with the load cell signals. Doing so can markedly improve the quality of raw data as well as the result in later processing. The equation of the median filter is:

$$y(i)=Med[x(i-N), \ldots, x(i), \ldots x(i+N)] \quad (0)$$

where x(i) is raw data at time i, N is the order of the filter and N=20.

Recognizing that the sum of the moments about laterally extending axes 80L and 80R equals zero and that the sum of the moments about longitudinally extending axes 80F and 80H also equals zero yields the following relationships in which "L" is the distance shown as $L_L$ in FIG. 5 and w is the distance shown as $W_L$ in FIG. 5.

$$(TM)(a) = \left(\frac{P_3}{\cos\alpha} + P_4\right)w \quad (1)$$

$$(TM)(w-a) = \left(\frac{P_1}{\cos\alpha} + P_2\right)w \quad (2)$$

$$(TM)(b) = \frac{P_1 + P_3}{\cos\alpha}\left(\frac{L}{2} + \frac{L}{2}\cos\alpha\right) \quad (3)$$

$$(TM)\left(\frac{L}{2} + \frac{L}{2}\cos\alpha - b\right) = (P_2 + P_4)\left(\frac{L}{2} + \frac{L}{2}\cos\alpha\right). \quad (4)$$

Therefore, $$\cos\alpha = (P1+P3)/(TM-P2-P4) \quad (5)$$

and therefore coordinates a and b are $$a = \frac{(P_3/\cos\alpha + P_4)w}{TM} = \frac{(TM\ P_3 - P2\ P3 + P1\ P4)w}{(P_1+P_3)w} \quad (6)$$

$$b = \frac{(P_1+P_3)(1+\cos\alpha)L}{2\ TM\cos\alpha} = \frac{(TM-P_2-P_4+P_1+P_3)L}{2\ TM} \quad (7)$$

Irrespective of whether the procedure branches from block 164 to block 166 or to block 168, it then advances to block 170. Block 170 outputs the value of a to a destination. Example destinations include display 116 of user interface 114 and memory 150 where the value can be accessed for use by other instructions.

Figure 7:
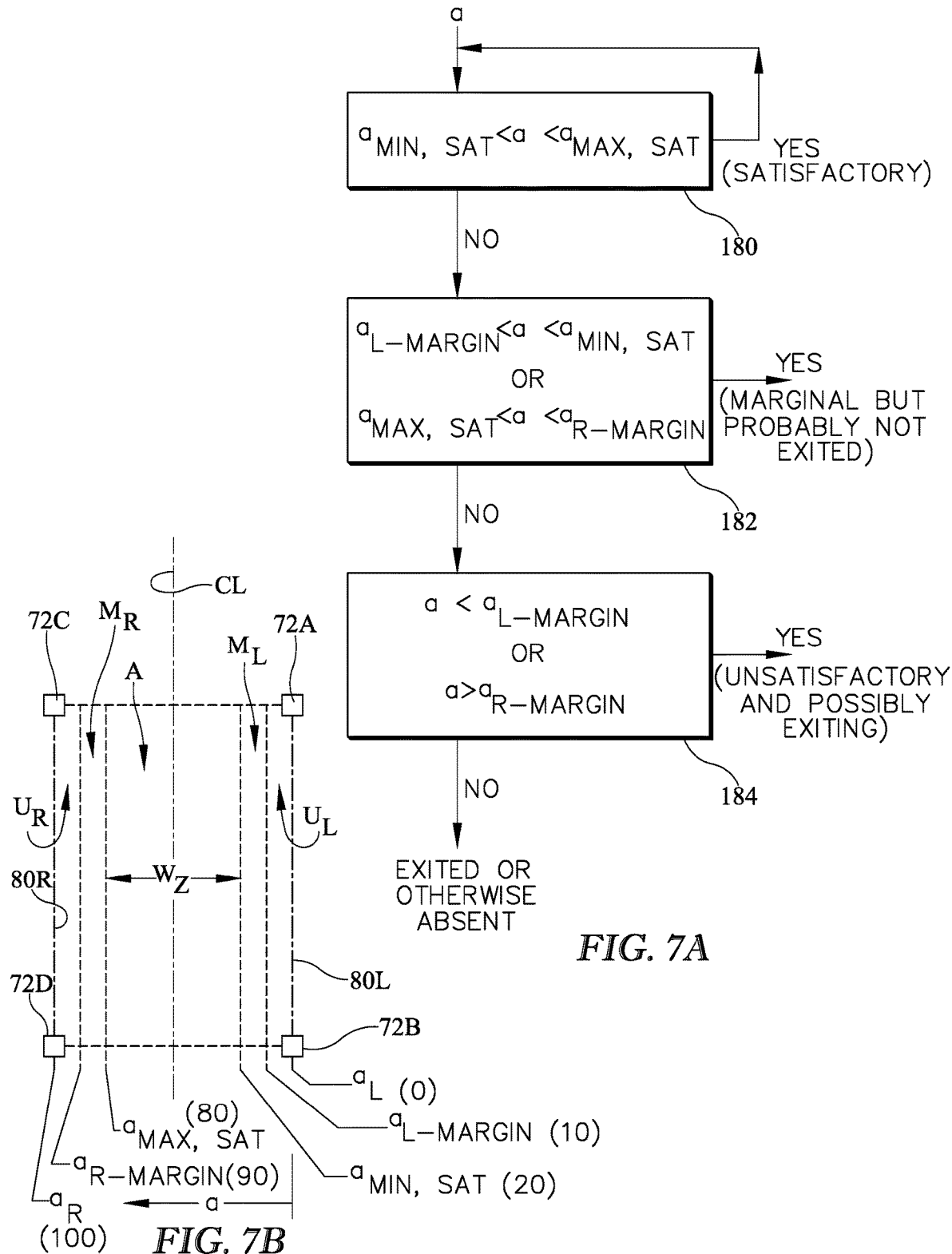
FIG. 7A is a block diagram showing a procedure by which the machine readable instructions may determine if the location of the occupant's center of gravity, CG is within or outside of an acceptable zone.
FIG. 7B is a plan view showing the acceptable zone of FIG. 7A and also showing zones that are other than acceptable.

The machine readable instructions may also include a group of instructions which cause the system to determine if the location of the occupant's center of gravity, CG is within or outside of an acceptable zone. FIG. 7A shows a block diagram of the procedure. FIG. 7B is a plan view similar to the plan view of FIG. 5 showing the load cells, an acceptable zone, and zones which are other than acceptable. FIG. 7B includes a scale indicating that a, the lateral location of the occupant's CG, is measured from notional line 80L. The scale also shows six coordinate values for a expressed symbolically. Example numerical values of a, expressed as a percentage of width $W_L$, are shown in parentheses. The percentage values can be converted to any convenient unit of measurement such as centimeters or inches. In one embodiment the distance $W_L$ is 870 mm and the acceptable zone extends laterally from a=220 mm to a=650 mm. The coordinate values and their significance are summarized in table 1 where "inboard" and "outboard" are relative terms indicating laterally closer to and laterally further away from centerline CL respectively.

TABLE 1

| Cooordinate "a" | Example value (percent) | Significance |
| --- | --- | --- |
| $a_L$ | 0 | coordinate of notional line 80L between the left load cells |
| $a_{L-MARGIN}$ | 10 | outboard border of left marginal zone |
| $a_{MIN,SAT}$ | 20 | left border of acceptable zone (inboard border of left marginal zone) |
| $a_{MAX,SAT}$ | 80 | right border of acceptable zone (inboard border of right marginal zone) |
| $a_{R-MARGIN}$ | 90 | outboard border of right marginal zone |
| $a_R$ | 100 | coordinate of notional line 80R between the right load cells |

Block 180 receives the value a, the lateral coordinate of the occupant's center of gravity as determined from equation (6) above. Block 180 tests whether the value of a is between the values of $a_{MIN,SAT}$ and $a_{MAX,SAT}$. If so, the occupant's center of gravity, and therefore the occupant herself, is considered to be in a satisfactory or acceptable zone A, and the procedure loops back and periodically carries out the same test. Zone A has a lateral width $W_Z$ and is symmetrical about centerline CL. Zone A is considered to be an acceptable zone because if the occupant's center of gravity falls within that zone, the occupant is too far away from the siderails for her position to be consistent with an impending egress attempt.

If the value of a is not between the values of $a_{MIN,SAT}$ and $a_{MAX,SAT}$ the procedure advances to block 182. Block 182 tests whether a falls within one of two marginal zones, zone $M_L$ laterally bordered by $a_{L-MARGIN}$ and $a_{MIN,SAT}$, and zone $M_R$ laterally bordered by $a_{MAX,SAT}$ and $a_{R-MARGIN}$. Zones $M_L$, $M_R$ are referred to as marginal zones because if the occupant's center of gravity, and therefore the occupant herself, falls within one of those zones she is close enough to one of the siderail assemblies to indicate that she may be intent on exiting the bed. However zones $M_L$, $M_R$ are nevertheless far enough away from the siderail assemblies to indicate that the occupant is probably still present in the bed.

If the value of a does not fall within either of the two marginal zones, the procedure advances to block 184. Block 184 tests whether a falls within one of two unsatisfactory zones, zone $U_L$ laterally outboard of $a_{L-MARGIN}$ and zone $U_R$ laterally outboard of $a_{R-MARGIN}$. Zones $U_L$, $U_R$ are referred to as unsatisfactory zones because if the occupant's center of gravity, and therefore the occupant herself, falls within one of those zones she is close enough to one of the siderail assemblies to indicate not only that she may be intent on exiting the bed, but that she may be in the act of exiting.

If the value of a does not fall within any of the zones, it is likely that the occupant has exited the bed or is otherwise absent (e.g. didn't get into the bed in the first place).

The terms "acceptable", "marginal" and "unsatisfactory" in the foregoing description are not value judgements, but instead are intended to assign reasonably descriptive terms to the zones to express the likelihood that an occupant is intent on exiting the bed if her center of gravity is in that zone. For example one might consider that zones $M_L$ and $M_R$, like zones $U_L$, $U_R$, are both unsatisfactory. In addition, quantities of zones other than the quantities disclosed herein may be desirable.

The block diagram of FIG. 7A can be truncated after any block which has provided the desired information about the location of the occupant's center of gravity. For example if it is desired to know whether or not the occupant is in the acceptable zone, and no further information is desired about the actual location of the occupant's center of gravity if she happens to be outside the acceptable zone, the block diagram can be truncated after block 180. This corresponds to FIG. 8 which shows only an acceptable zone A flanked by unacceptable zones $U_L$, $U_R$. The block diagram, truncated after block 180, would follow the "YES" loop as long as the occupant's center of gravity were in acceptable zone A. If the occupant's center of gravity were not in zone A, the procedure would issue a notification of that fact, but would not seek to establish anything else about the actual location of the occupant's center of gravity.

Figure 8:
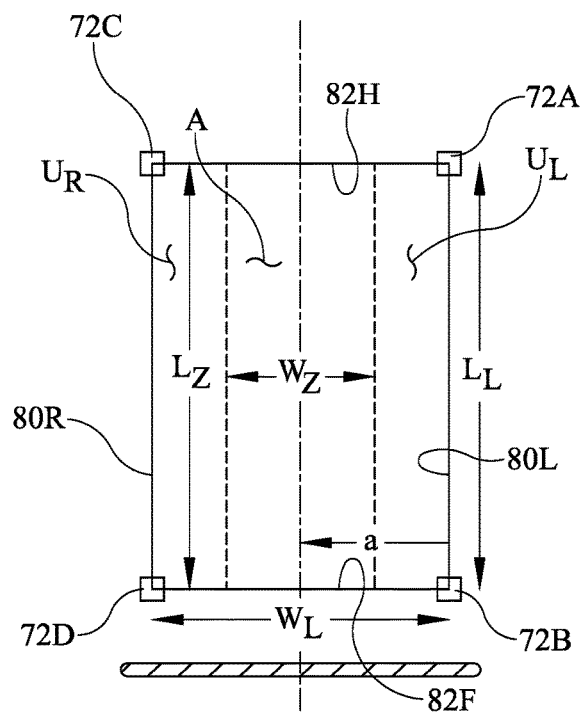
FIGS. 8-11 are plan views illustrating variations on the shape and longitudinal length of the acceptable zone.

Continuing to refer to FIG. 8, the width $W_Z$ of the acceptable zone A is substantially uniform in the longitudinal direction. Zone A extends longitudinally from notional line 82H for a distance $L_Z$ substantially equal to the distance $L_L$ between the left load cells 72A, 72B or between the right load cells 72C, 72D.

Figure 9:
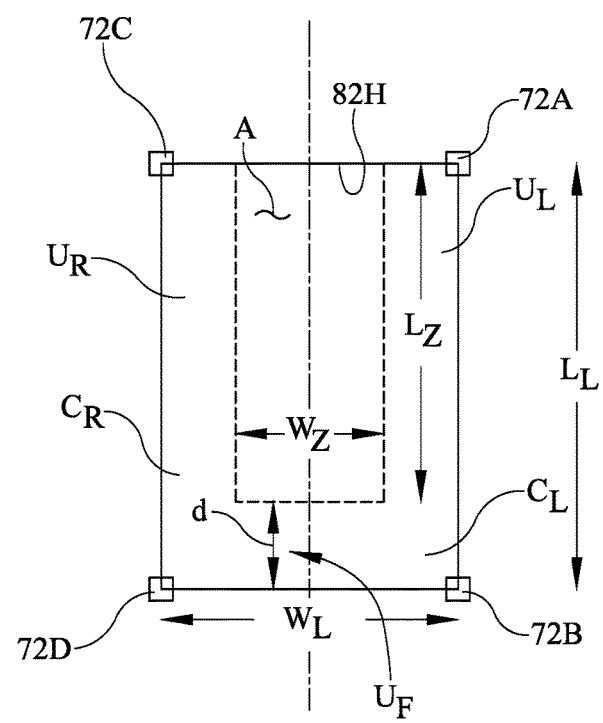

FIG. 9 shows a variant in which the width $W_Z$ of the acceptable zone A is substantially uniform in the longitudinal direction but the length $L_Z$ of zone A is less than the distance $L_L$ between the left or right load cells. The adjustment to the length of the of the acceptable zone is carried out by processor 134 to account for the fact that in FIG. 9 footboard 112 is absent (in contrast to FIG. 8 where it is present). The adjustment reflects the belief, represented in the logic of the processor, that the absence of the footboard may invite the occupant to egress from the foot end of the bed rather than from one of the sides. Accordingly, acceptable zone A is longitudinally foreshortened in comparison to its length in FIG. 8 by distance d so that the unacceptable zone includes a foot region $U_F$ in addition to flank regions $U_L$ and $U_R$. Corner regions $C_L$ and $C_R$ may be considered to be part of the foot regions or part of the flank regions.

Figure 10:
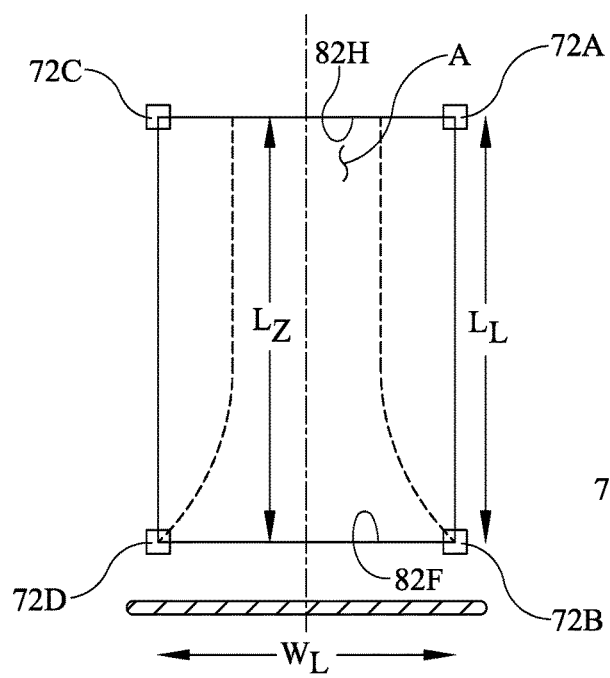

FIG. 10 shows a variant in which zone A extends longitudinally from notional line 82H for a distance $L_Z$ substantially equal to the distance $L_L$ between the left or right load cells and in which width $W_Z$ of acceptable zone A is not substantially uniform in the longitudinal direction. The flare at the foot end of zone A reflects the belief that when footboard 112 is present, an occupant is less likely to exit from the sides of the bed at a location near the footboard and more likely to exit from the sides of the bed at a location more remote from the footboard.

Figure 11:
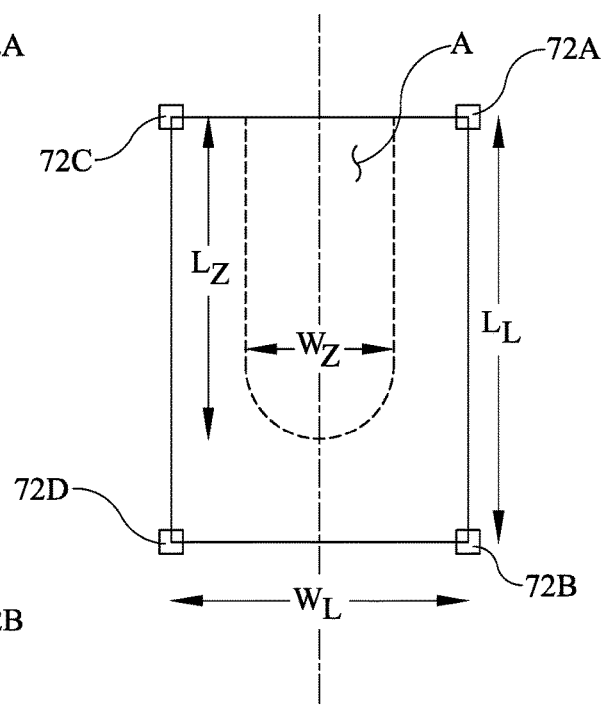

FIG. 11 shows a variant in which length $L_Z$ of zone A is less than the distance $L_L$ between the left or right load cells and in which width $W_Z$ of acceptable zone A is not substantially uniform in the longitudinal direction but instead diminishes at the foot end of the zone.

In general, factors such as the physical activity habits and the size and shape of the patient may be taken into account in defining the acceptable zone.

As noted previously the positions of the siderails define a variety of siderail configurations, some of which are exit deterrent, and some of which are exit accommodating. In one variant the processor monitors the siderail positions, assesses the degree to which the corresponding siderail configuration is exit deterrent or exit accommodating, and automatically adjusts the width $W_z$ of the acceptable zone depending on the detected siderail configuration. If the siderail configuration is highly exit deterrent the processor defines an acceptable zone whose width is relatively large. If the siderail configuration is highly exit accommodating the processor defines an acceptable zone whose width is relatively small. The width adjustment can be applied to either a zone of substantially uniform width or to a zone of nonuniform width. The width adjustment may also transform a constant width zone to a nonconstant width zone and vice versa.

Figure 12A:
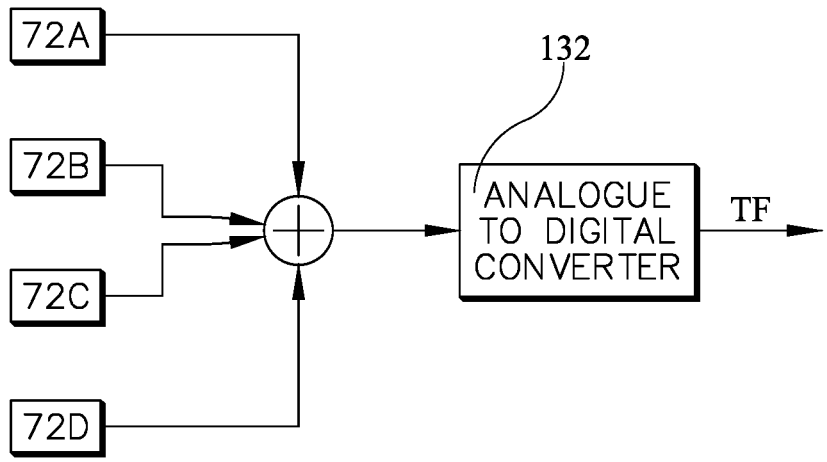
FIGS. 12A and 12B are diagrams showing options for the order in which load cell output signals are combined and converted to digital signals.
Figure 12B:
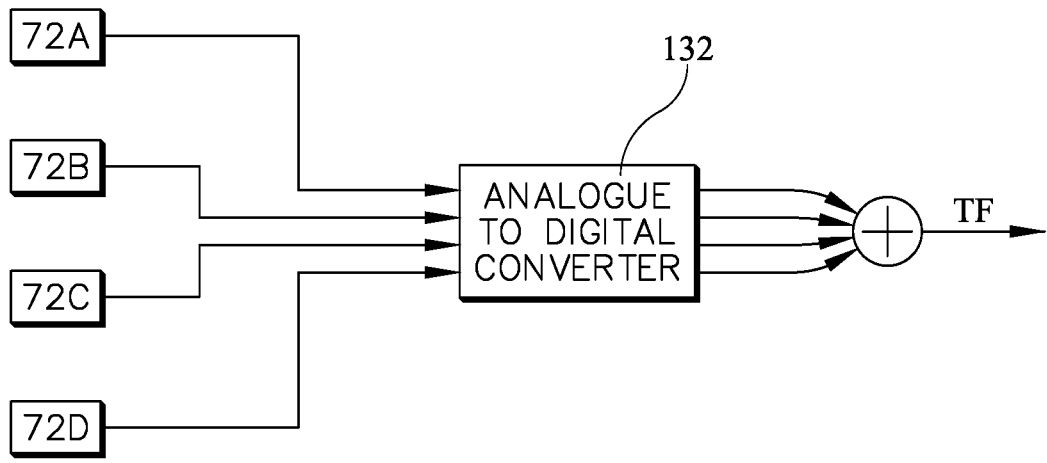

Referring to FIGS. 12A, 12B, 13, and 14, the machine readable instructions 150 stored in memory 136 cause the system to perform actions aimed at predicting occupant exit from an occupant support. The following explanation is in the form of an example for a bed with four load cells (e.g. 72A, 72B, 72C, 72D). The example assumes that the load cells have been zeroed so that their outputs represent only forces attributable to the occupant. The example also assumes that the signal analyzed in order to make the prediction reflects the combined outputs of all four load cells as seen in FIG. 12A or 12B. In FIG. 12A the load cell signals are combined, and the combined signal is then converted from analog to digital. Alternatively, as seen in FIG. 12B, each load cell signal is first converted from analog to digital, then the digital signals are combined.

Figure 13:
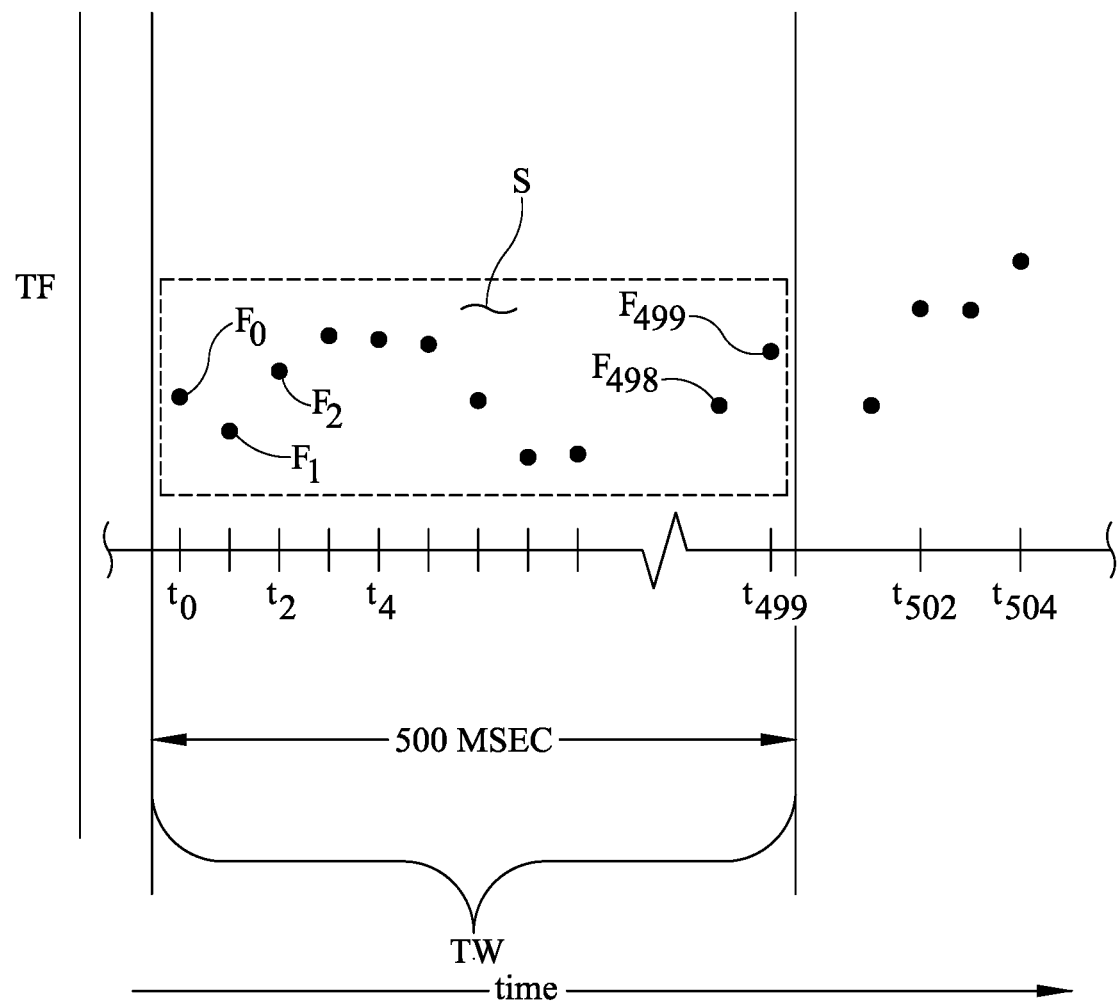
FIG. 13 is a graph of an example digital signal corresponding the total force exerted on the load cells.

Referring to FIG. 13, the system operates on a signal S which is a collection of discrete data readings of the total force TF exerted on the load cells. The example signal S is made up of 500 individual force readings, $F_0, F_1, \ldots F_{499}$, representing a time window TW of 500 msec. The force determinations are temporally spaced from each other by 1 msec.

The real-time signals collected from the four load cells take the form of a dynamic time series that contains various values varying from time to time. Thus the signals are usually high dimensional. In order to reduce computational complexity and explore the similarity of the intrinsic mechanism of the time series, statistical features or characteristics, carrying summarized information and global structure, are extracted to form a fixed-length vector as a substitution for the load cell signals. Such feature extraction can be seen as a dimension-reduction process that plays an important role in improving the classification precision. The statistical features should be sensitive to the patient's actions, the action severity and type. Different feature vectors represent different signals that correspond to various actions on the bed. Fisher Discriminant Analysis (FDA) is applied to the vectors to determine some typical patterns.

FDA is a kind of algorithm based on multivariate statistical analysis. It is one of the most popular techniques extensively studied in pattern classification and has shown excellent performance in some specific fields like fault detection and diagnosis. Compared with Principal Component Analysis (PCA), FDA is proven to have advantages to some degree that takes the information between classes into account and is optimal in terms of maximizing the separation among classes as far as possible. More concretely, FDA aims to determine a set of transformation vectors, or in other words, projection directions, on which the scatter within each class is minimized while the scatter of data points from different classes is maximized.

Denote p as the number of classes, N as the number of observations, J as the number of measurement variables (so the fixed-length vector extracted from the load cell signals is J-dimensional in this case). It does not matter if the number of observations is different in different classes while the number of variables should be kept the same. Then let $X_i$ ($N_i \times J$) be the data matrix that is composed of the set of samples belonging to Class i in which the vector of the measurement variables for the $i^{th}$ observation is represented as $X_i$, where $N_i$ is the number of observations in that class. It should be noted that the vector is always a column vector when there is no statement to the contrary.

The within-class scatter matrix for class i can be defined by:

$$S_i = \sum_{x_i \in X_i} (x_i - \bar{x}_i)(x_i - \bar{x}_i)^T \qquad (8)$$

where $\bar{x}_i(J \times 1)$ is the J-dimensional mean vector for Class i, and where $$\bar{x}_i = \frac{1}{N_i} \sum_{x_i \in X_i} x_i. \qquad (9)$$

So the within-class scatter matrix for all the classes is:

$$S_w = \sum_{i=1}^{p} S_i \qquad (10)$$

Then the between-class scatter matrix is calculated as:

$$S_b = \sum_{i=1}^{p} N_i (\bar{x}_i - \bar{x})(\bar{x}_i - \bar{x})^T \qquad (11)$$

where $\bar{x}$ is the mean vector for all the observations in all classes.

The total-scatter matrix is $$S_t = \sum_{i=1}^{N} (x_i - \bar{x})(x_i - \bar{x})^T$$

and is equal to the sum of $S_w$ and $S_b$.

The separation among classes is defined as the ratio of the between-class scatter $S_b$ to the within-class scatter $S_w$, and $S_w$ is assumed invertible, $$\Delta(w) = \frac{w^T S_b w}{w^T S_w w} \qquad (12)$$

where w denotes the Fisher optimal projection direction.

Then the problem is transformed to calculating the vector w that maximizes the function $\Delta(w)$, i.e., the projected data are the best separated. By the method of Lagrange multipliers, it is easy to deduce the following equation when $S_w$ is non-singular.

$$S_w^{-1} S_b w = \lambda w \tag{13}$$

Here we can get a conventional eigenvalue problem that $\lambda$ is the eigenvalue of the matrix $S_w^{-1} S_b$ and the vector w is the corresponding eigenvector. In fact, it can also be proved that $\lambda$ is equal to $\Delta(w)$ which indicates the degree of the separability among all the classes. As a result, the above conditional extremum problem finally goes to calculating the maximum eigenvalue and eigenvector with regard to $S_w^{-1} S_b$. Since the rank of $S_b$ is less than p, the number of non-zero eigenvalues will be not more than p−1, and FDA only focuses on informative eigenvectors in these directions.

Denoting a as the matrix that contains all the informative eigenvectors $w_1, w_2, \ldots, w_a$, then the discriminant function can be described as:

$$g_i(x) = -\frac{1}{2}(x - \bar{x}_i)^T W_a \left( \frac{1}{n_i - 1} W_a^T S_i W_a \right)^{-1} W_a^T (x - \bar{x}_i) + \tag{14}$$

$$\ln(P_i) - \frac{1}{2} \ln \left[ \det \left( \frac{1}{n_i - 1} W_a^T S_i W_a \right) \right]$$

where $P_i$ is the prior probability for class i, and can be omitted for convenience when the probability is same for each class.

A new observation x can be assigned to Class i when $$g_i(x) > g_j(x) \forall j \neq i \tag{15}$$

The FDA algorithm is applied to the load cell signals when the patient is found to be near the edge, in which case what is needed is to determine whether the action of the patient is dangerous or not. So, the problem can be seen as a two-class discrimination problem that aims to classify the signals into two class: action that suggests an exit event or not, i.e., moving or stationary. Therefore, only one direction w can be obtained and presented as:

$$w = \frac{1}{d} S_w^{-1} (\bar{x}_1 - \bar{x}_2) \tag{16}$$

where the intermediate parameter d is defined by:

$$d = (\bar{x}_1 - \bar{x}_2)^T S_w^{-1} (\bar{x}_1 - \bar{x}_2) \tag{17}$$

Then all the observations can be projected to one-dimension space and we can easily classify the new data by Mahalanobis distance.

Figure 24:
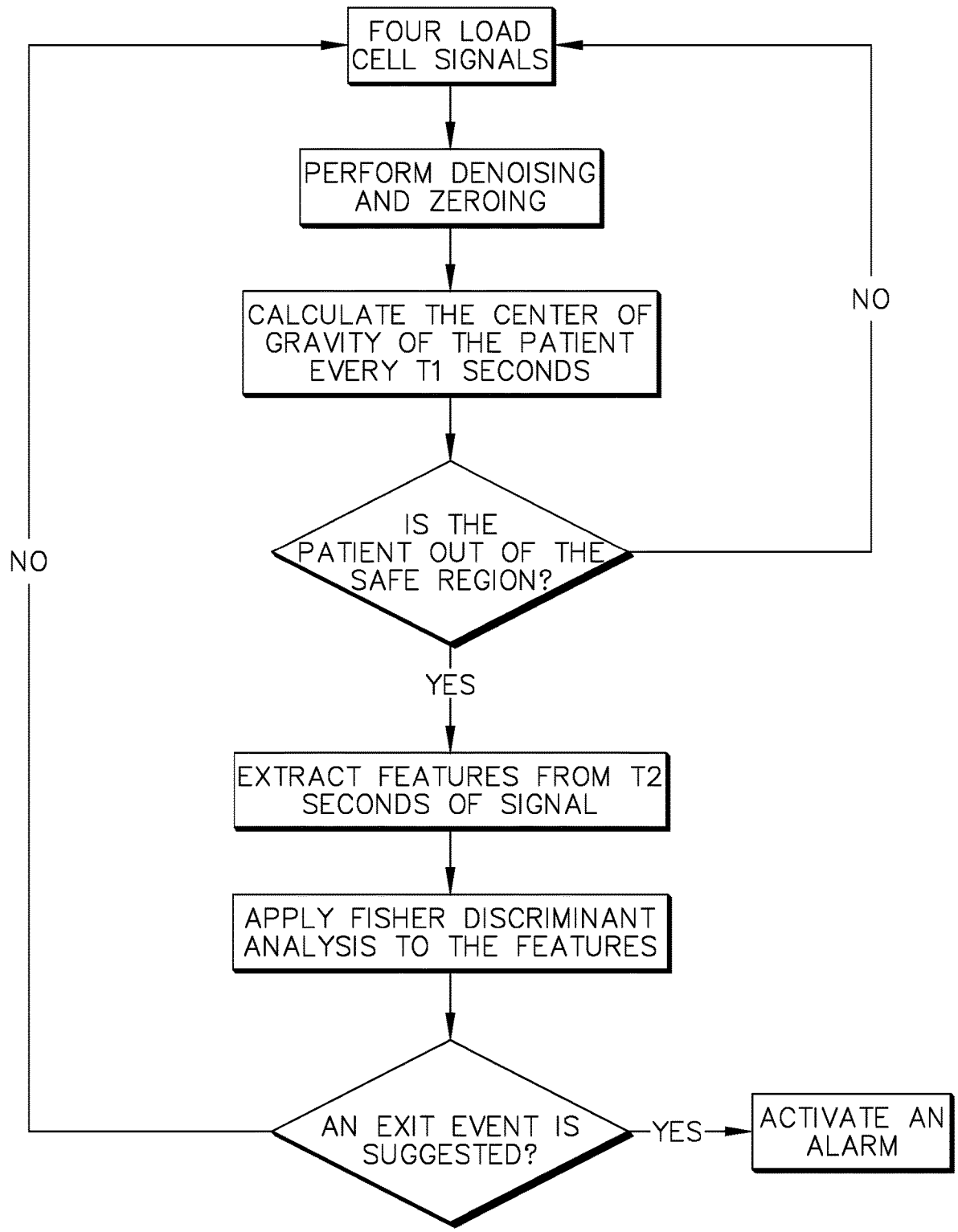
FIG. 24 is a block diagram showing a procedure by which the machine readable instructions generate a notification of a predicted bed exit event based on the load cell signals.

FIG. 24 is a flowchart showing an embodiment of the procedure of detecting an unauthorized bed-exit event based on load cell signals.

A sliding window with fixed length is used along the time direction. If the sampling frequency is f, then the length of the sliding window equals T2×f, and its step length is T1×f. The sliding window consecutively updates signals and always captures the latest information about the patient. Another parameter, counter, that is not shown in FIG. 24 can be used to further eliminate the peak interference in signals and enhance reliability of the system. The patient is identified out of the safe region at time t only if the continuous values of the parameter X that include X(t−counter+ 1), . . . , X(t−1), X(t) all have exceeded the threshold. The sensitivity of the proposed method can be adjusted by changing the value of T1,T2 and counter etc.

Figure 25:
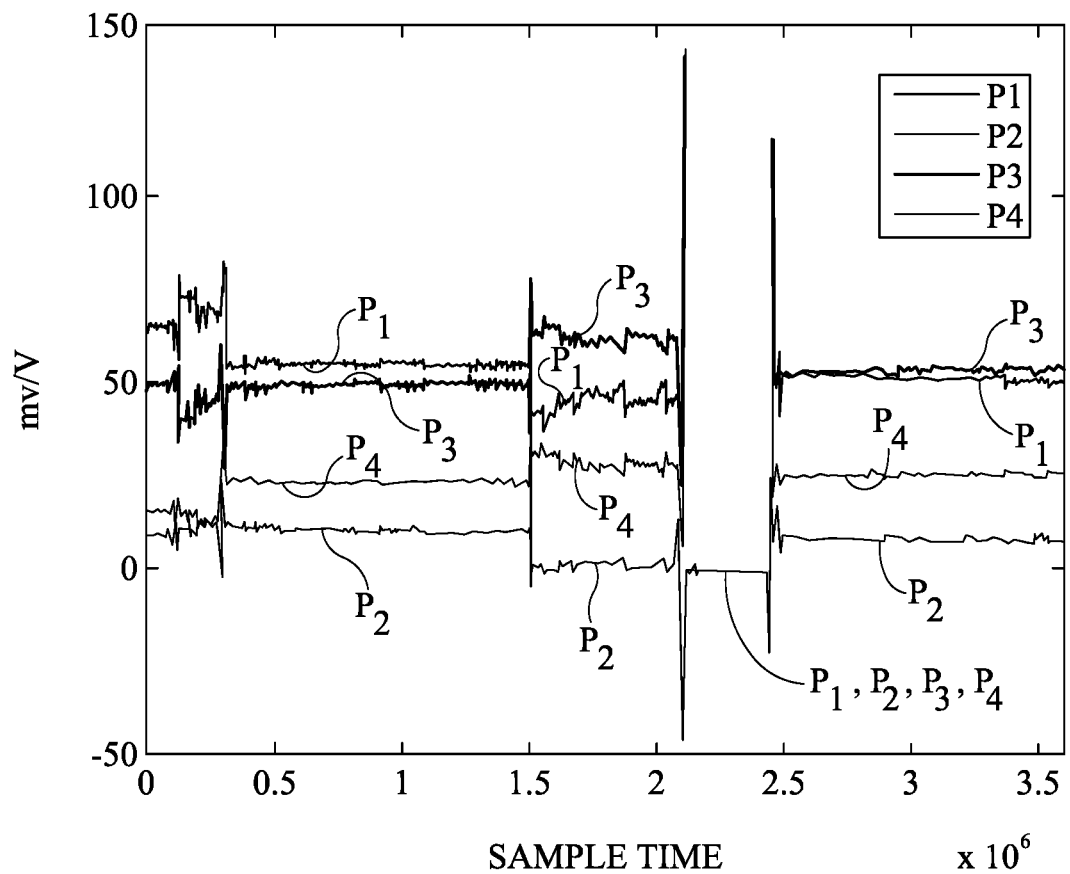
FIGS. 25-26 show results of a one hour test using a volunteer who occupied a bed and was free to exit the bed at any time.
Figure 26:
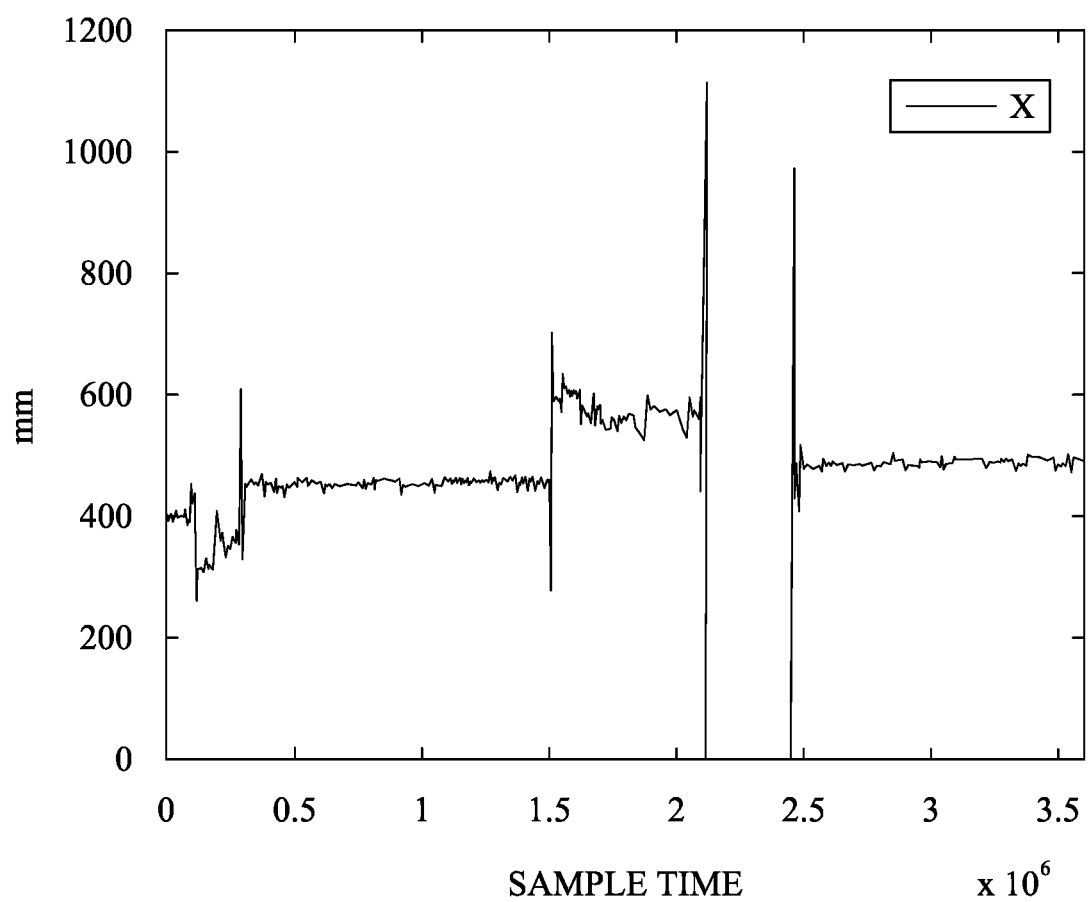

FIGS. 25-26 show results of a one hour test using a volunteer who occupied a bed and was free to exit the bed at any time. The time scale on FIG. 25 and FIG. 26 is in milliseconds (1 hour=3,600,000 msec.). FIG. 25 shows the signal values after smoothing, filtering and initializing. Some fluctuation in the signals shows the volunteer's movement. The parameters T1 and T2 of the sliding window are set to be 0.1 and 2 respectively. So the coordinate X (which is "a" in FIGS. 5 and 7B) that indicates the position of patient is calculated every 0.1 seconds. FIG. 26 shows the value of X during this one hour time. The vertical axis of FIG. 26 has units of millimeters where 0 mm corresponds to line 80L of FIG. 5 and 870 mm corresponds to line 80R of FIG. 5. The acceptable zone extends from 220 mm to 650 mm. According to the principle of the calculation noted previously, the patient has already exited the bed when X equals 0. It is obvious that the volunteer has only exited the bed once during the experiment. Moreover, counter=10.

In the process of feature extraction, standard deviation and peak energy after Fast Fourier Transform (FFT) are selected from time domain and frequency domain respectively, to serve as a dimensional reduction for representing original signals. Whenever a new observation arrives, the two features are extracted from a time series containing data points in 2 seconds and then the observation is classified as either moving or stationary. An alarm will be activated when a state of dangerous moving is detected.

Figure 14:
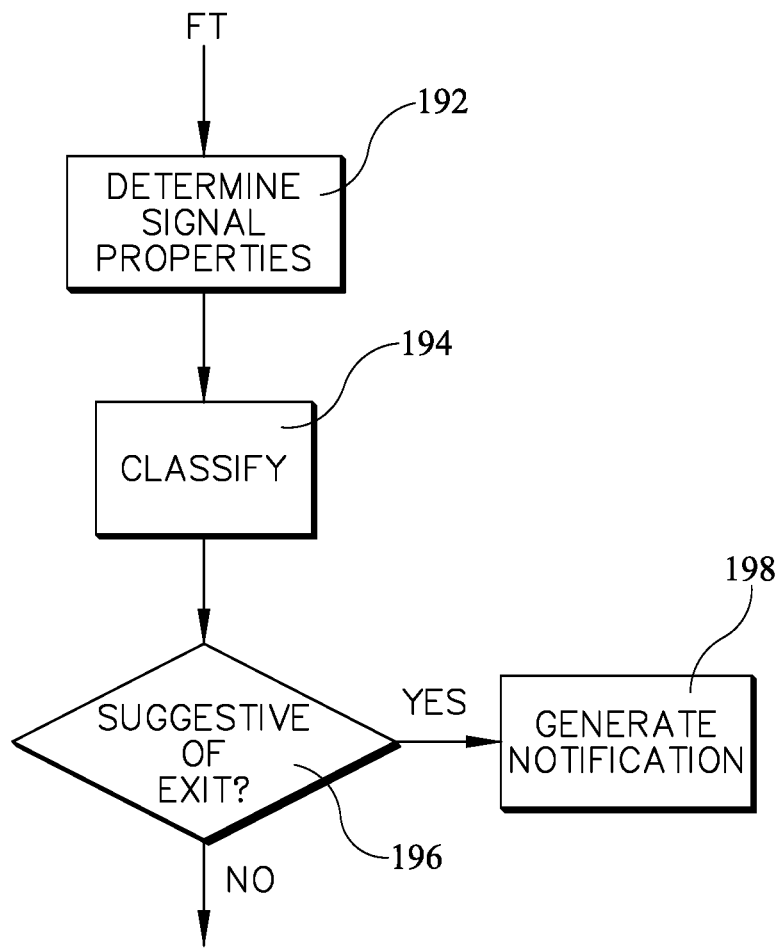
FIG. 14 is a block diagram showing a procedure by which the machine readable instructions generate a notification of a predicted bed exit event based on classifying a property of a load cell signal.

FIG. 14 is a block diagram showing an embodiment of a procedure by which the machine readable instructions can generate a notification of a predicted bed exit event based on classifying a property of a load cell signal. Block 192 of FIG. 14 determines one or more properties of the signal during the time interval of time window TW. The determined properties may include the mean frequency, the median frequency, the peak frequency, and the standard deviation of frequency of the time domain signal, and the mean energy of the signal during a specified time interval. Additionally or alternatively, the determination may include establishing the Fourier transform of S in order to determine the frequency spectrum of S. In one embodiment applicable to discrete data readings the determination includes establishing the Discrete Fourier Transform (DFT), for example by using a Fast Fourier Transform (FFT) algorithm. The determined properties of the frequency domain may include the mean frequency, the median frequency, the peak frequency, the standard deviation of frequency, and the mean energy of the signal during a specified time interval.

Block 194 classifies the property or properties as suggesting an exit event or as not suggesting an exit event. The classification may be carried out on frequency domain properties and/or time domain properties by Fisher Discriminant Analysis (FDA). FDA projects an observation with several properties to one-dimension space. FDA can be thought of as a way to assign different weights to different properties and to carry out the classification with general consideration of all properties involved. Alternatively or additionally the classification may be carried out by comparing each time domain and/or frequency domain property to an exit criterion, and, if the property matches the criterion, classifying the property as indicating an exit event. A property matches a criterion if it bears a predesignated relationship to the criterion. For instance, the mean frequency may be considered to match a mean frequency criterion if the mean frequency is less than the mean frequency criterion; the median frequency may be considered to match a median frequency criterion if the median frequency is less than the median frequency criterion; the peak frequency may be considered to match a peak frequency criterion if the peak frequency is greater than the peak frequency criterion; the standard deviation may be considered to match a standard deviation criterion if the standard deviation is greater than the standard deviation criterion; and the mean energy may be considered to match a mean energy criterion if the mean energy during a specified time interval is greater than the mean energy criterion.

The classification can also be based on some combination of time and frequency domain properties. One example of such a classification is based on mean value, median value, peak value and standard deviation in the frequency domain, and standard deviation of frequency in the frequency domain. Mean energy of the signal may also be used as a property.

At block 196 the system responds to whether or not the classification is suggestive of occupant exit. The response is based on the classification of block 194. If the classification at block 196 suggests that the occupant is intent on exiting the bed, the system proceeds to block 198 and generates a notification, specifically a notification of a predicted exit. Example notifications include sounding a local alarm, sending an alert message to a nearby nurses' station and illuminating a warning light.

If multiple properties are classified by comparison to criteria, the notification can be a function of how many of the properties match their respective criteria. In one example the notification of a predicted exit is generated only if the mean frequency, the median frequency, the peak frequency, the standard deviation, and the mean energy all match their respective criteria. More generally, the system includes at least two force sensors whose outputs are combined (e.g. as in FIG. 12A or 12B). The machine readable instructions classify N signal properties (in the examples presented herein, N=5 (mean frequency, median frequency, peak frequency, standard deviation of frequency and mean energy)). A notification of predicted exit is generated only if all N signal properties match their respective criteria.

In another example the notification is generated if at least one of the mean frequency, the median frequency, the peak frequency, the standard deviation, and the mean energy match their respective criteria. More generally, the system includes at least two force sensors whose outputs are combined (e.g. as in FIG. 12A or 12B). The machine readable instructions classify N signal properties (in the examples presented herein, N=5 (mean frequency, median frequency, peak frequency, standard deviation of frequency and mean energy)). A notification of predicted exit is generated if at least one of the N signal properties matches its respective criterion.

In yet another variant a weighting factor can be applied to the presence or absence of a match between each property and its criterion in order to reflect a belief that some properties are more reliable or important than others in predicting an exit event.

Figure 15:
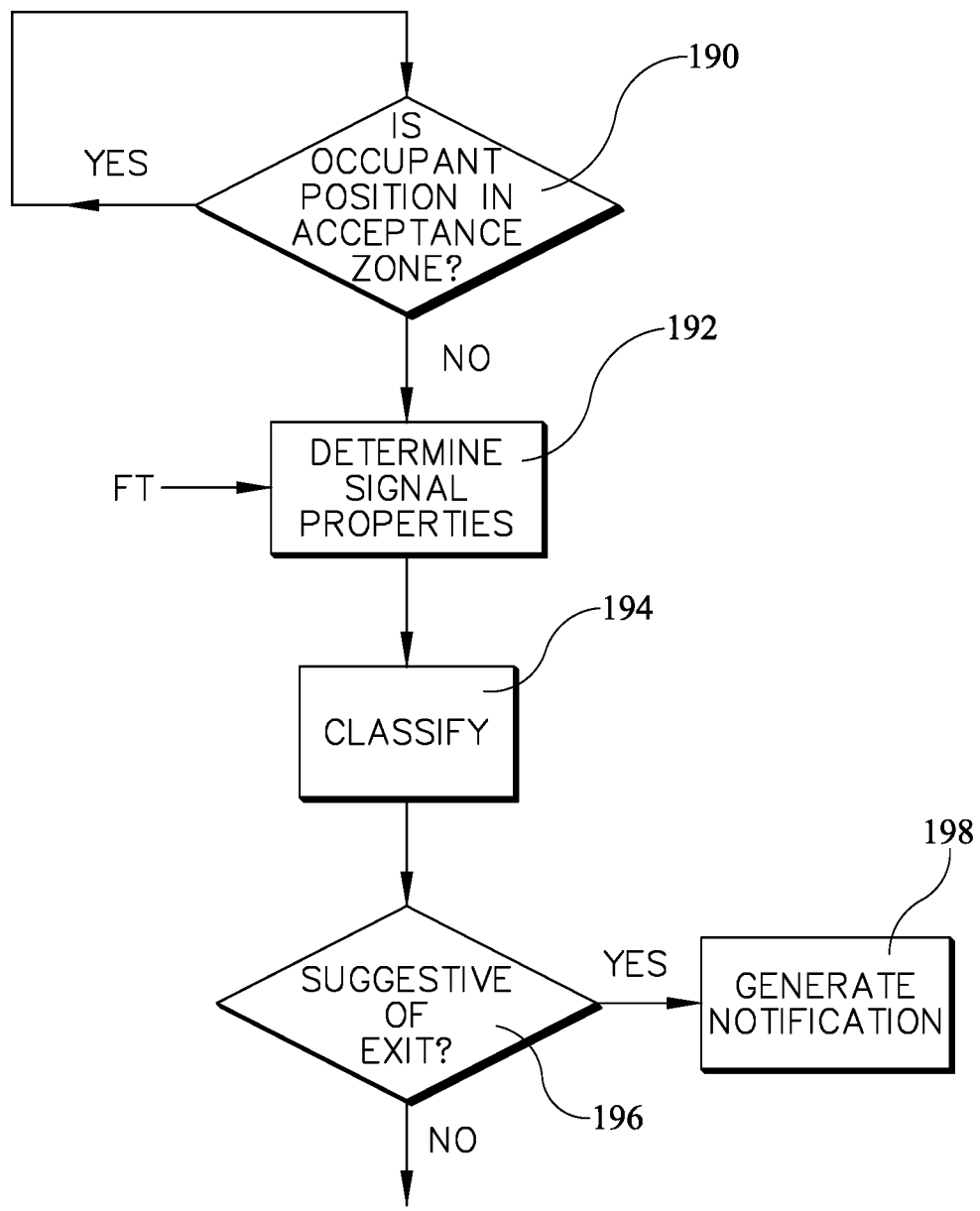
FIG. 15 is a block diagram similar to that of FIG. 14 including an additional step of testing whether or not the occupant center of gravity calculation indicates that the occupant is within an acceptable zone.

FIG. 15 is a variant of the block diagram of FIG. 14. FIG. 15 is the same as FIG. 14 in all respects except for the inclusion of occupant position assessment block 190. Block 190 tests whether or not the occupant center of gravity calculation indicates that the occupant is within an acceptable zone such as zone A of FIGS. 7B and 8-12. If the occupant is within the acceptable zone the determining, classifying and generating steps of blocks 192, 194, 198 are not carried out. In other words the determining, classifying and generating steps are carried out only if the center of gravity is outside the acceptable zone.

Figure 16:
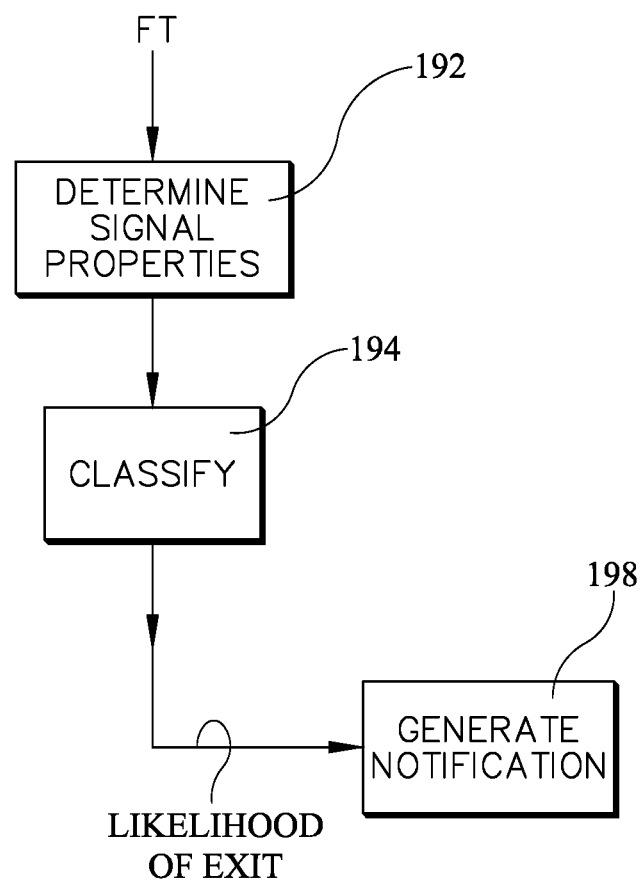
FIG. 16 is a block diagram similar to that of FIG. 14 showing a procedure by which the machine readable instructions unconditionally generate a notification of the likelihood or probability of occupant exit based on the outcome of the classification.

FIG. 16 is another variant of the block diagram of FIG. 14. In FIG. 14, the response at block 196 depends on a YES or NO answer as to whether the the outcome of the classification at block 194 is suggestive of occupant exit. A notification is generated only if the answer is YES. By contrast FIG. 16 shows the notification being generated unconditionally at block 198. For example the notification could be a probability ranging from zero percent to 100 percent, or could be a signal to illuminate a green light if the likelihood of exit is low, a yellow light if the likelihood of exit is moderate, and a red light if the likelihood of exit is high.

The block diagram of FIG. 16 could also be modified to include an occupant position assessment such as block 190 of FIG. 15.

Figure 17:
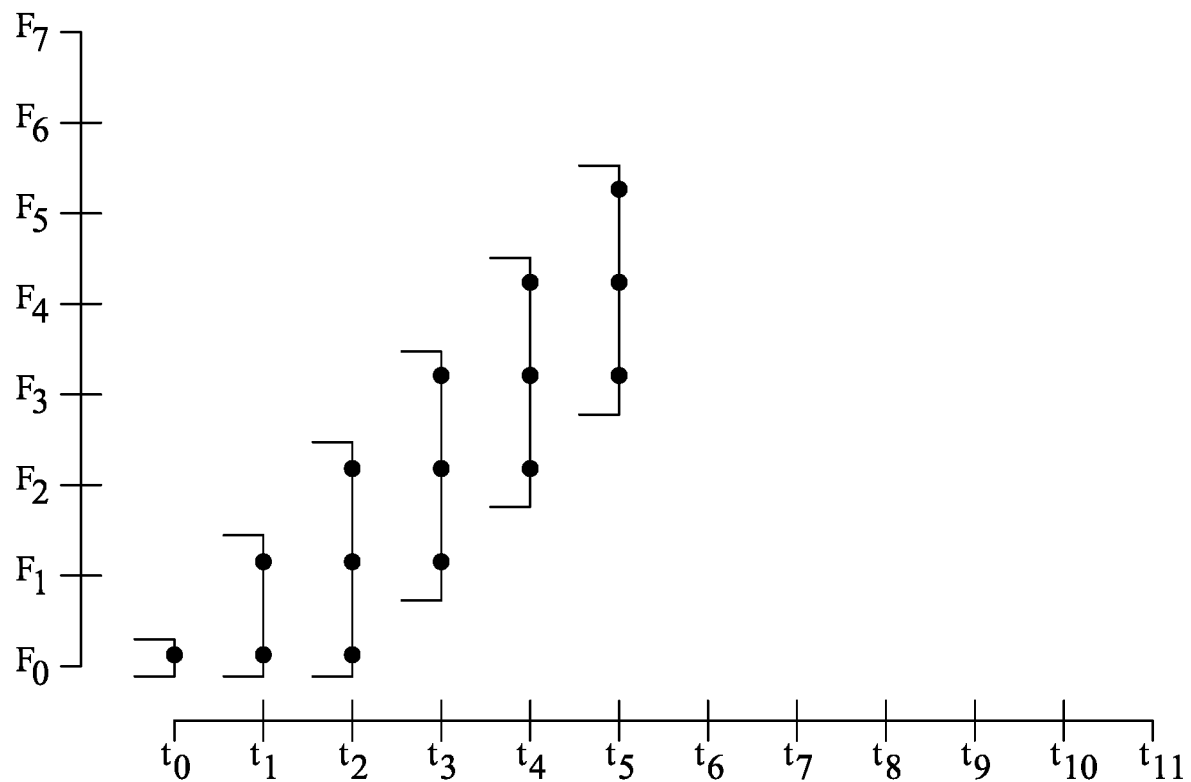
FIG. 17 is a graph showing a sliding window for defining the time and force coordinates which make up a segment of a signal to be analyzed to predict occupant exit from a bed.

Returning now to FIG. 13, example signal S is made up of a sample of 500 force determinations from a 500 msec time window TW. As time passes the window progresses to the right (or equivalently, the time coordinates progress to the left) so that the property or properties determined at block 192 of FIGS. 14-16 are based on the most recent information. In one embodiment window TW is a sliding window which slides 1 msec. forward in time for each 1 msec. passage of time. In other words the content of the window is updated every sampling interval. For example if signal S embraces t0 through $t_{499}$ at time $t_{499}$, it would embrace $t_1$ through $t_{500}$ at time $t_{500}$, $t_2$ through $t_{501}$ at time $t_{501}$ and so forth. When the data collection is initialized the window does not slide until it first expands sufficiently to capture the required number of data points. This concept is illustrated in the separate, simplified example of FIG. 17 where the window initially expands to embrace three force determinations at three time coordinates and then slides forward one time coordinate every sampling interval.

Figure 18:
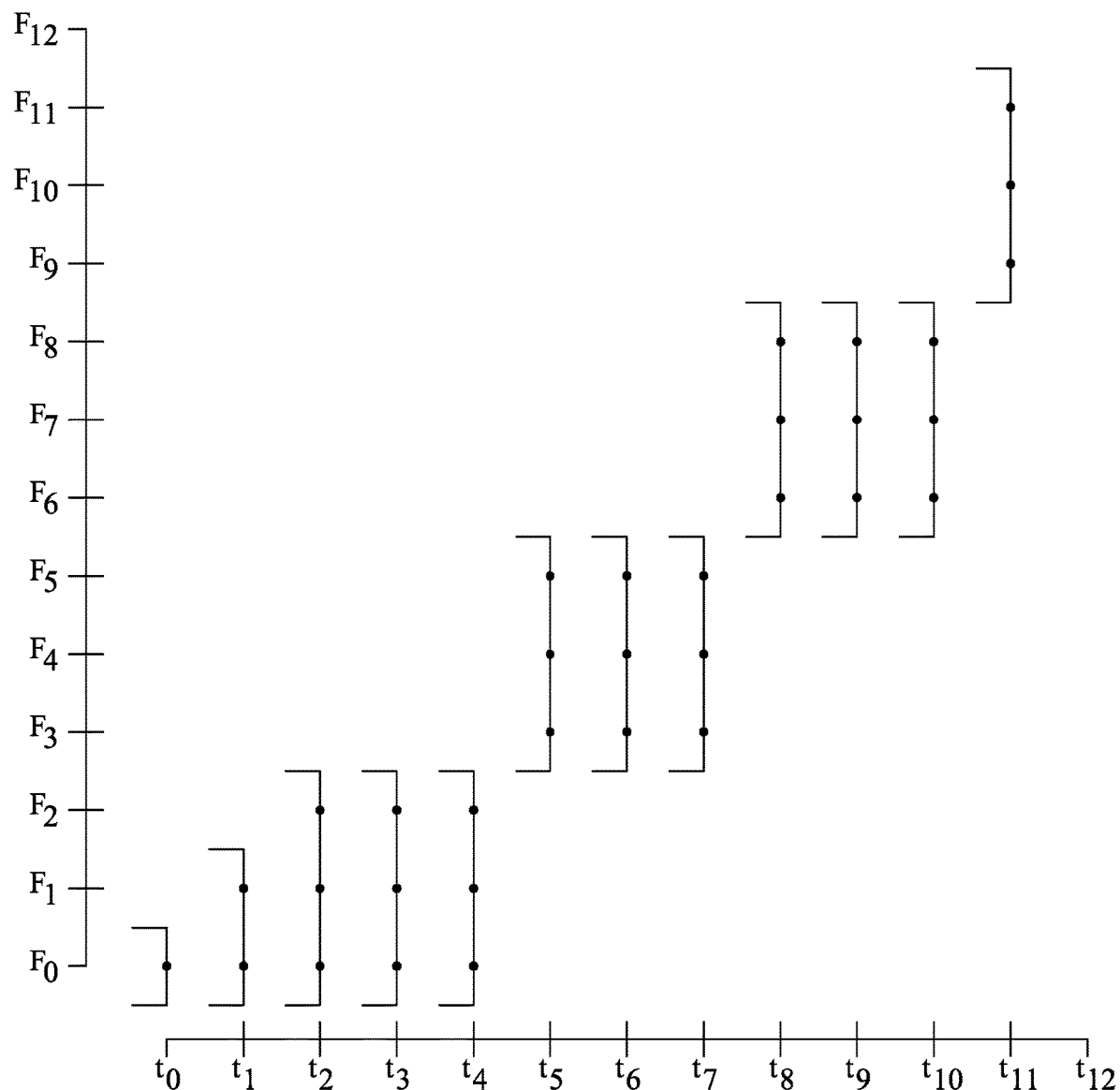
FIG. 18 is a graph showing a stepwise window for defining the time and force coordinates which make up a segment of a signal to be analyzed to predict occupant exit from a bed.

Referring additionally to FIG. 18, in another embodiment window TW is a stepwise window. i.e a window that advances in a stepwise fashion to replace multiple data readings with a like quantity of more current readings. The window initially expands the same way as the window of FIG. 17 until it embraces three force readings $F_0$, $F_1$, $F_2$ associated with the first three time coordinates $t_0$, $t_1$ and $t_2$. The window then continues to embrace the three force readings $F_0$, $F_1$, $F_2$ from the first three time coordinates $t_0$, $t_1$ and $t_2$ until three more recent force readings ($F_3$ from $t_3$, $F_4$ from $t_4$ and $F_5$ from $t_5$) are all available at time $t_5$. The window then steps forward three time intervals, relinquishing the force values $F_0$, $F_1$, $F_2$ from $t_0$, $t_1$ and $t_2$ and capturing the force values $F_3$, $F_4$, $F_5$ from times for $t_3$, $t_4$ and $t_5$. The sensitivity of the system can be adjusted by changing the width of the time window, the sampling rate, and, if the location of the occupant's CG is accounted for, the frequency with which that location is calculated.

The discussion and examples presented so far employ aggregated information from all of the load cells (four load cells in the examples) as seen in FIGS. 12A and 12B. However the outputs from the load cells can be considered individually. The horizontal axis of FIG. 19 distinguishes between generating a notification of exit only if the properties of the signals from all the load cells match their respective criteria and generating a notification of exit even if the properties from only some (least one but fewer than all) of the load cells match their respective criteria. The vertical axis of FIG. 19 distinguishes between generating a notification of exit only if all the properties of the signals from the load cells under consideration match their respective criteria and generating a notification even if only if some of the properties (least one but fewer than all) from the load cells under consideration match their respective criteria.

Figure 19:
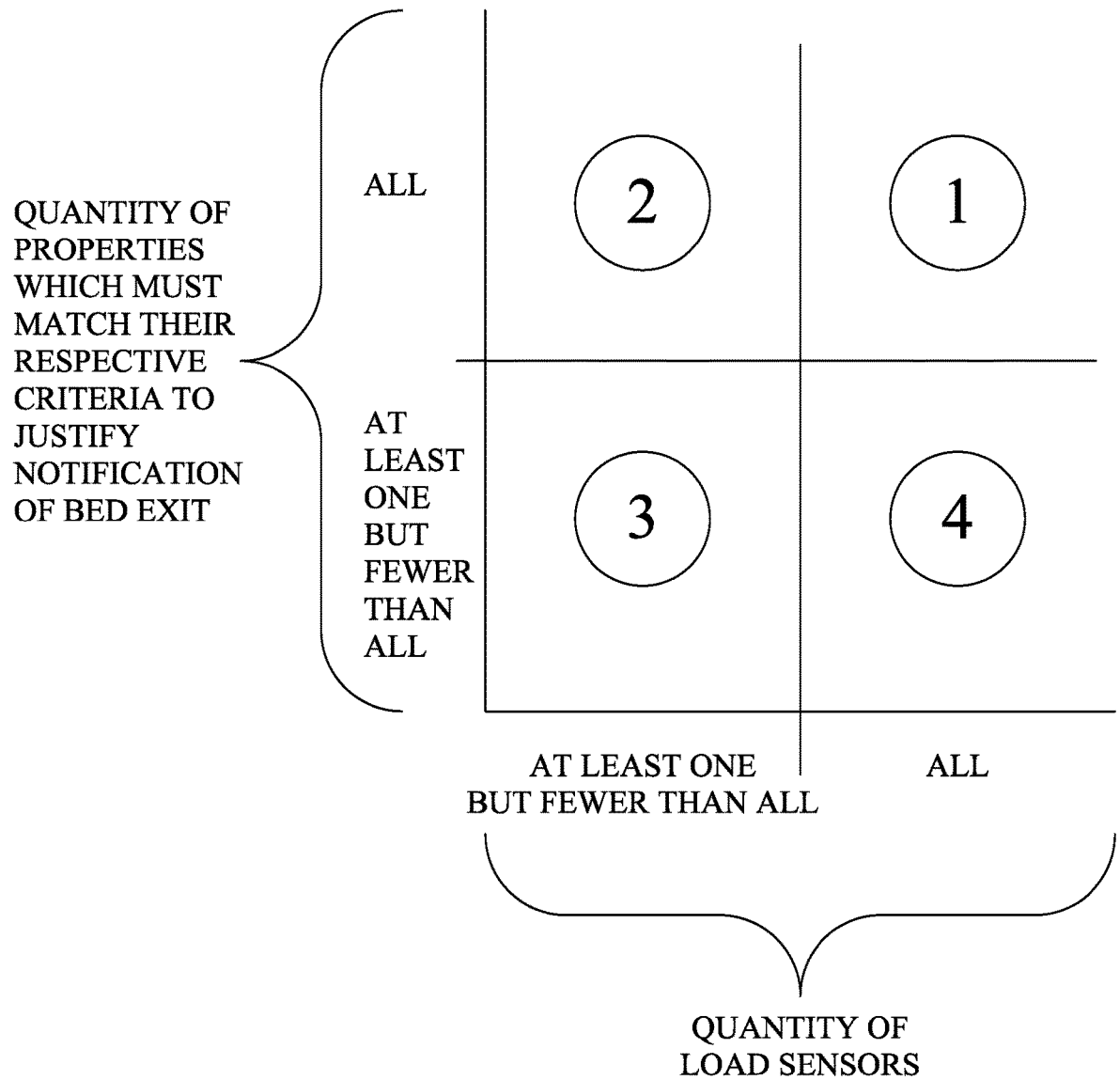
FIG. 19 is a graph summarizing a range of options for the quantity of load sensors whose signal properties must match a criterion and the quantity of signal properties which must match a criterion in order for the system to declare that a bed occupant is intent on exiting the bed.
Figure 20:
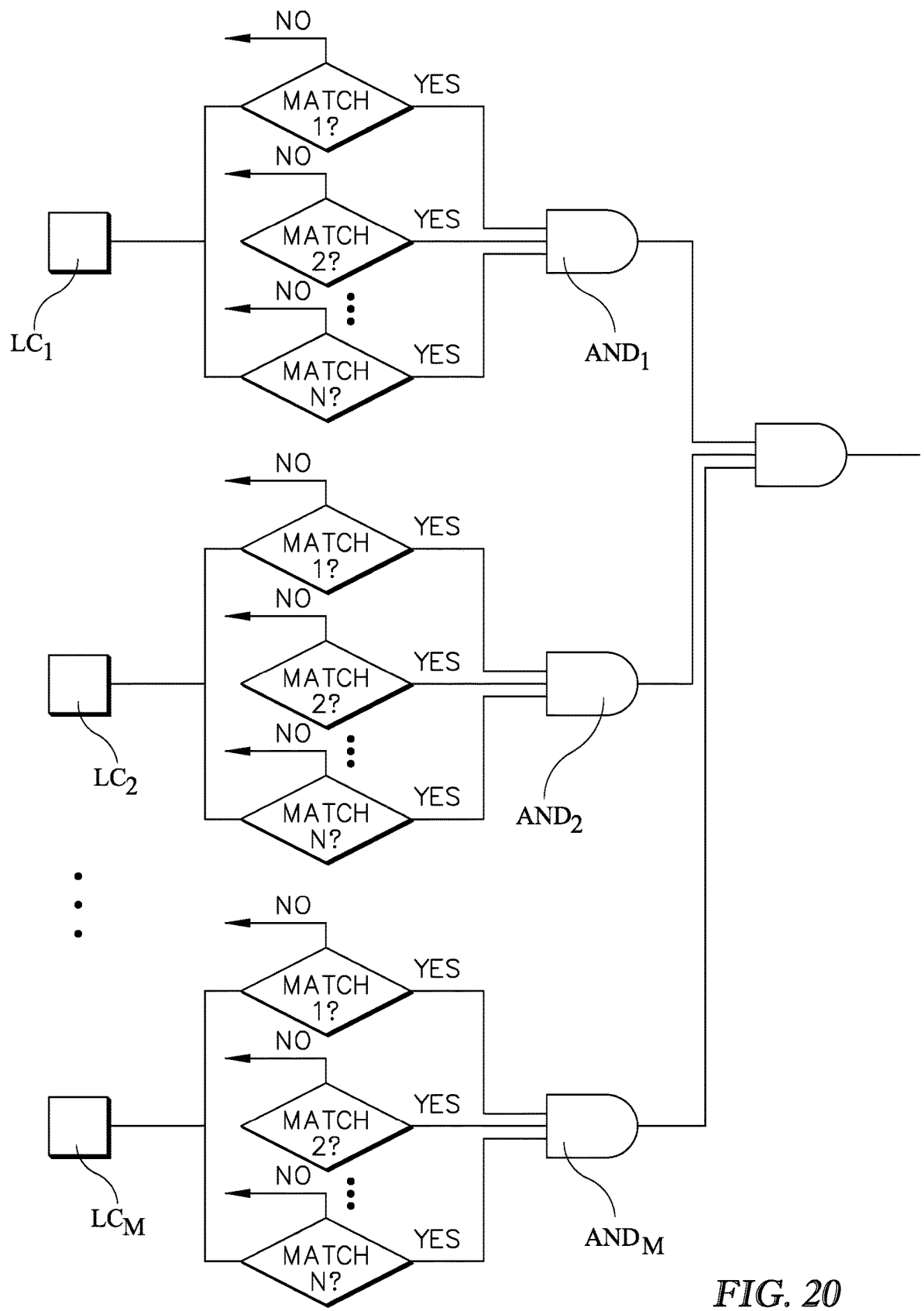
FIGS. 20-23 are logic diagrams further detailing the options of FIG. 19.

FIG. 20 corresponds to quadrant 1 of FIG. 19. The system includes least two force sensors such as load cells $LC_1$ through $LC_M$. The machine readable instructions determine and classify N signal properties from each of the M load cells. A notification of a predicted exit is generated only if all N signal properties from all M sensors match their respective criteria. This is indicated by the array of AND gates.

Figure 21:
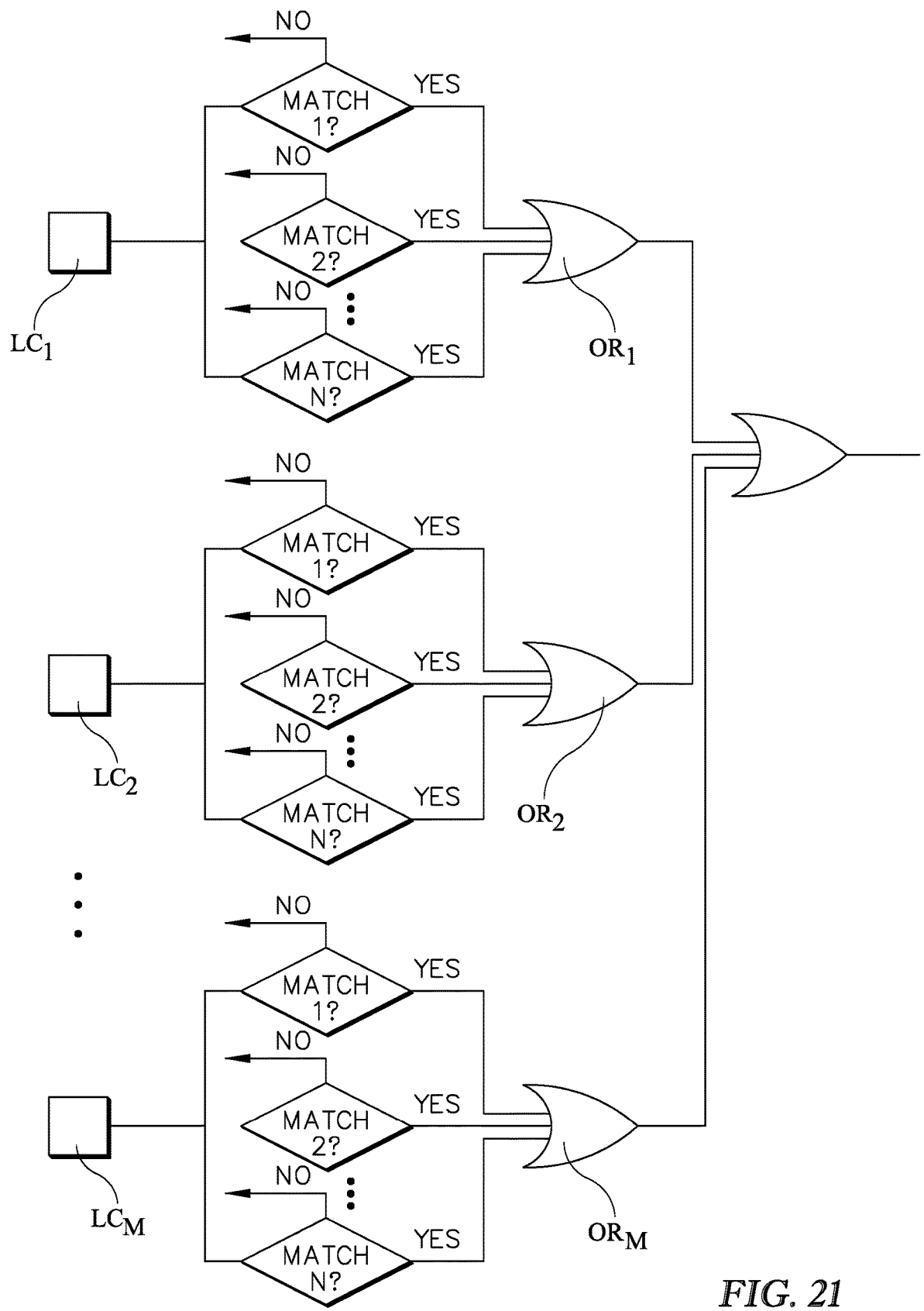

FIG. 21 corresponds to quadrant 3 of FIG. 19. A notification of a predicted exit is generated if at least one of the N signal properties from at least one of the M sensors matches its respective criterion. This is indicated by the array of OR gates.

In the system of FIG. 21 there is no requirement that the matching property or properties be the same for all the load cells that yield a match. For example the signal from load cell $LC_1$ could yield a match for the mean and median criteria while the signal from load cell $LC_2$ yields a match for standard deviation. The corresponding OR gates will both produce a TRUE output. Alternatively, it could be required that the matched signal property be the same property for all of the sensors which yield a match. This could be accomplished, for example, by setting the outputs of OR gates 1 through M to FALSE if the "same property" criterion were not met.

Figure 22:
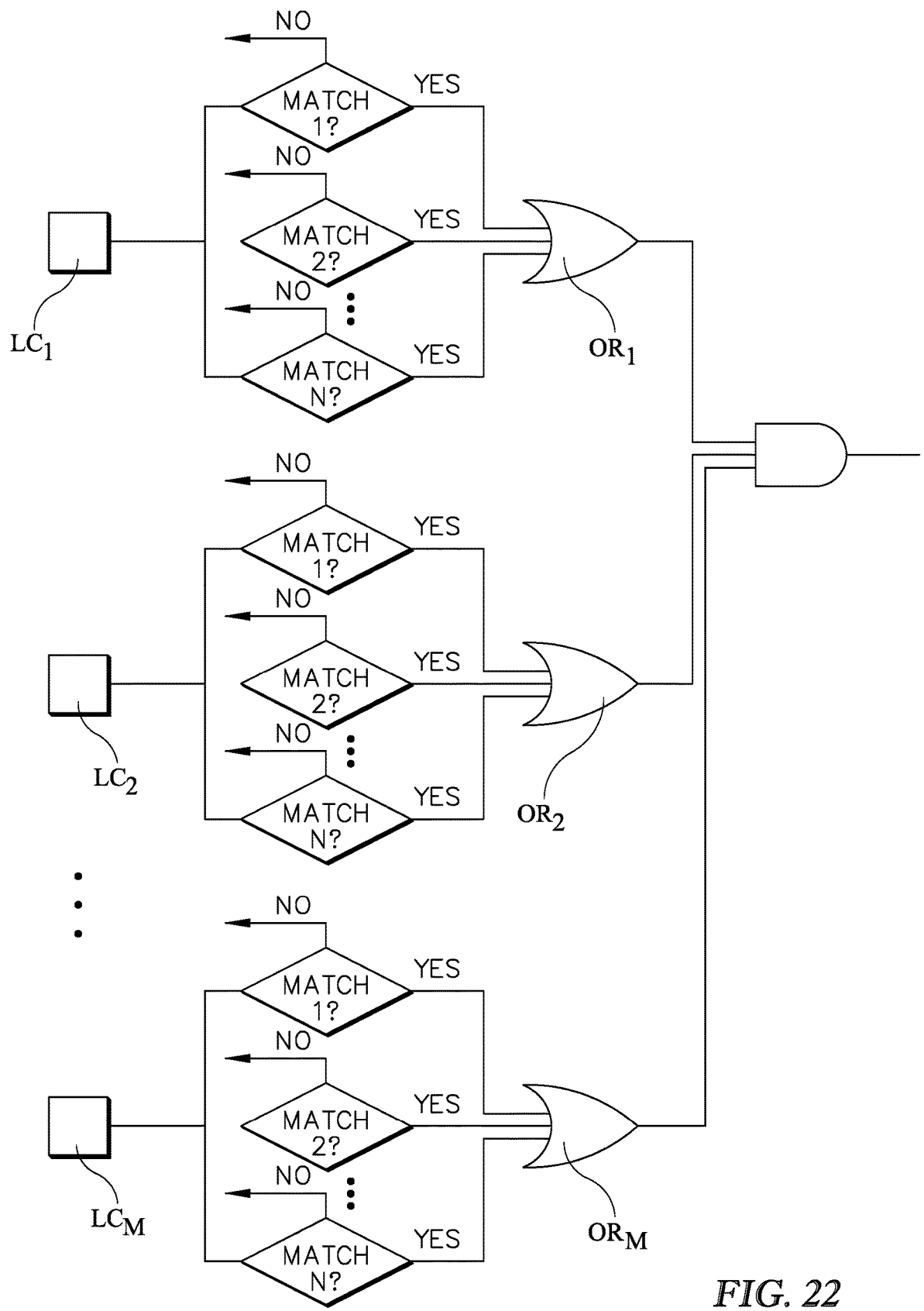

FIG. 22 corresponds to quadrant 4 of FIG. 19. A notification is generated if at least one of the N signal properties from each and every one of the M load cells matches its respective criterion. This is shown by the combination of OR gates and AND gates. Each of the M OR gates produces a TRUE output if any one of the signal properties from the Mth load cell matches its criterion. Therefore for any given load cell only one of the signal properties needs to match its criterion in order for the output of the corresponding OR gate to be TRUE. However the AND gate produces a TRUE value only if all the OR gates yield a TRUE output.

In the system of FIG. 22 there is no requirement that the matching property or properties be the same for all the load cells that yield a match. For example the signal from load cell $LC_1$ could yield a match for the mean and median criteria while the signal from load cell $LC_2$ yields a match for standard deviation. The corresponding OR gates will both produce a TRUE output. Alternatively, it could be required that the matched signal property be the same property for all of the at least two load cells which yield a match. This could be accomplished, for example, by setting the outputs of OR gates 1 through M to FALSE if the "same property" criterion were not met.

Figure 23:
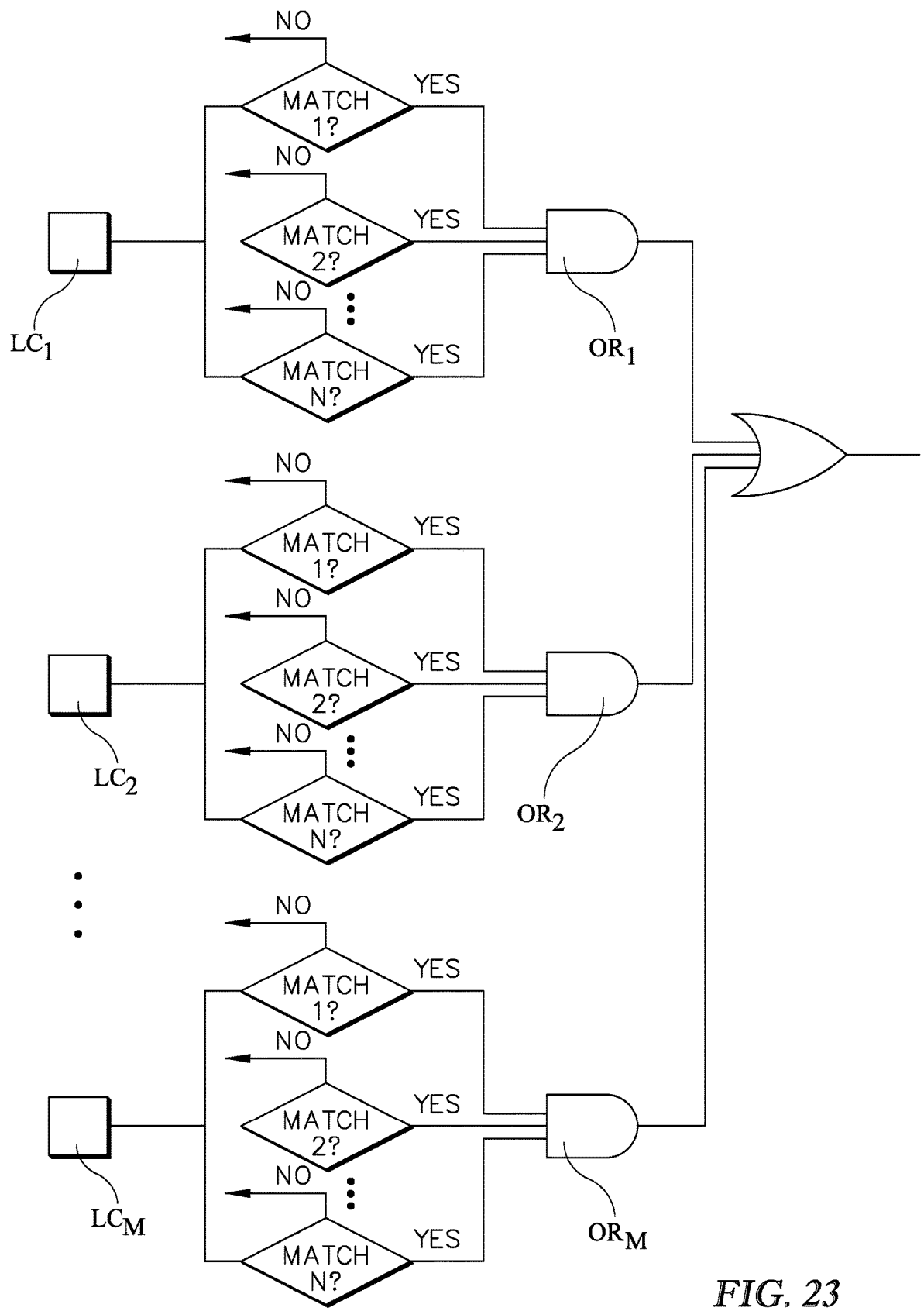

FIG. 23 corresponds to quadrant 2 of FIG. 19. A notification is generated only if all the N signal properties from at least one of the M sensors match their respective criteria. This is shown by the combination of AND gates and OR gates. Each AND gate produces a TRUE output only if all the signal properties from the associated load cell match their respective criteria. The OR gate produces a TRUE output if any one of those AND gates produces a TRUE output.

The terms "substantially" and "about" may be used herein to represent the inherent degree of uncertainty that may be attributed to any quantitative comparison, value, measurement or other representation. These terms are also used herein to represent the degree by which a quantitative representation may vary from a stated reference without resulting in a change in the basic function of the subject matter at issue.

This disclosure expresses certain relationships as "greater than" (>) or "less than" (<). However the relationships could instead have been expressed as "greater than or equal to" (≥) or "less than or equal to" (≤) with no material effect on the outcome. Accordingly, as used in this specification including the claims, "greater than" (>) and "greater than or equal to" (≥) should be understood to be equivalent to each other. Similarly, "less than" (<) and "less than or equal to" (≤) should be understood to be equivalent to each other.

Although this disclosure refers to specific embodiments, it will be understood by those skilled in the art that various changes in form and detail may be made without departing from the subject matter set forth in the accompanying claims.

What is claimed is:

1. A system for predicting exit from an occupant support, the system comprising:
   a processor;
   a memory in communication with the processor;
   a frame having at least one force sensor which outputs a force signal in response to force exerted thereon; and
   machine readable instructions stored in the memory which cause the system to perform at least the following actions when executed by the processor:
      determine a property of the signal during an interval of time;
      classify the property as suggesting an exit event or as not suggesting an exit event; and
      if the property is classified as suggesting an exit event, generate a notification thereof;
   wherein the classifying step comprises:
      a) comparing the property to an exit criterion; and
      b) if the property matches the criterion, classifying the property as an exit event;
   wherein:
      the signal is in the form of or is converted to digital samples;
      the property of the signal is at least one of mean frequency, median frequency, peak frequency, standard deviation of frequency, and mean energy; and
      the exit criterion to which the property is compared is a mean frequency criterion, a median frequency criterion, a peak frequency criterion, a standard deviation of frequency criterion, and a mean energy criterion respectively;
      wherein the notification is generated only if the mean frequency, the median frequency, the peak frequency, the standard deviation, and the mean energy all match their respective criteria.

2. The system of claim 1 wherein the classifying step is carried out by Fisher Discriminant Analysis.

3. The system of claim 2 wherein the classifying step is carried out in the time domain and/or the frequency domain.

4. The system of claim 1 wherein the classifying step is carried out in the time domain and/or the frequency domain.

5. The system of claim 1 wherein:
   the mean frequency matches the mean frequency criterion if the mean frequency is less than the mean frequency criterion;
   the median frequency matches the median frequency criterion if the median frequency is less than the median frequency criterion;
   the peak frequency matches the peak frequency criterion if the peak frequency is greater than the peak frequency criterion;

the standard deviation matches the standard deviation criterion if the standard deviation is greater than the standard deviation criterion; and the mean energy matches the mean energy criterion if the mean energy during a specified time interval is greater than the mean energy criterion.

6. The system of claim 1 wherein the actions executed by the processor include determining whether the location of the center of gravity of the occupant is within an acceptable zone and:
not carrying out at least one of the determining, classifying and generating steps if the center of gravity of the occupant is within the acceptable zone; and
carrying out the determining, classifying and generating steps only if the center of gravity of the occupant is outside the acceptable zone.

7. The system of claim 6 wherein the acceptable zone has a width $W_Z$ which is non-uniform in a longitudinal direction of the frame.

8. The system of claim 6 further including:
a left siderail assembly comprising at least one left siderail mounted on the frame;
a right siderail assembly comprising at least one right siderail mounted on the frame;
each siderail being positionable at at least a deployed position and a stowed position, the positions of the siderails defining a siderail configuration, and wherein the acceptable zone has a width, and the processor adjusts the zone width as a function of the siderail configuration.

9. The system of claim 8 wherein the zone width is non-uniform in a longitudinal direction of the frame for at least one siderail configuration.

10. The system of claim 6 further including:
a footboard installable on and removable from a foot end of the frame, and wherein the acceptable zone has a width and the processor adjusts the width of the acceptable zone as a function of whether or not the footboard is installed on the frame.

11. The system of claim 1 wherein the at least one force sensor comprises at least two force sensors and wherein the machine readable instructions determine and classify N signal properties and wherein the notification is generated only if classification of all N signal properties from all the sensors suggest an exit event.

12. The system of claim 1 wherein the interval of time corresponds to a sliding time window.

13. The system of claim 1 wherein the interval of time corresponds to a stepwise time window.

14. The system of claim 1 wherein the property suggesting an exit event comprises a center of gravity of the occupant being outside of an acceptable zone defined with respect to the occupant support, wherein the acceptable zone has a shape other than a quadrilateral shape.

15. The system of claim 1 wherein the machine readable instructions implement a median filter on the signal prior to the classifying step to remove noise from the signal.

16. The system of claim 1 wherein the notification includes an indication of a probability from zero to 100 percent of the exit event occurring.

17. The system of claim 1 wherein the notification includes illumination of lights of different colors to indicate low, moderate, and high likelihoods of the exit event occurring.

* * * * *